(12) United States Patent
Kimura

(10) Patent No.: US 11,324,438 B2
(45) Date of Patent: May 10, 2022

(54) INFORMATION PROCESSING APPARATUS, INFORMATION PROCESSING METHOD, AND NON-TRANSITORY COMPUTER-READABLE MEDIUM FOR ACQUIRING AND DISPLAYING A SKIN CONDITION ANALYSIS RESULT BASED ON AN EPIDERMIS IMAGE

(71) Applicant: Sony Corporation, Tokyo (JP)

(72) Inventor: Natsuki Kimura, Tokyo (JP)

(73) Assignee: Sony Corporation, Tokyo (JP)

( * ) Notice: Subject to any disclaimer, the term of this patent is extended or adjusted under 35 U.S.C. 154(b) by 572 days.

(21) Appl. No.: 15/303,270

(22) PCT Filed: Apr. 8, 2015

(86) PCT No.: PCT/JP2015/060925
§ 371 (c)(1),
(2) Date: Oct. 11, 2016

(87) PCT Pub. No.: WO2015/159767
PCT Pub. Date: Oct. 22, 2015

(65) Prior Publication Data
US 2017/0119301 A1 May 4, 2017

(30) Foreign Application Priority Data
Apr. 18, 2014 (JP) .............................. JP2014-086916

(51) Int. Cl.
*A61B 5/00* (2006.01)
*G06T 7/00* (2017.01)
(Continued)

(52) U.S. Cl.
CPC ............ *A61B 5/441* (2013.01); *A61B 5/0077* (2013.01); *A61B 5/743* (2013.01); *G06T 7/0012* (2013.01);
(Continued)

(58) Field of Classification Search
CPC ....... A61B 5/441; A61B 5/743; A61B 5/0077; A61B 2576/02; A61B 5/1079;
(Continued)

(56) References Cited

U.S. PATENT DOCUMENTS

| | | | | |
|---|---|---|---|---|
| 2004/0146290 A1* | 7/2004 | Kollias | ................... | G03B 29/00 396/14 |
| 2008/0045818 A1* | 2/2008 | Wood | ................... | A61B 5/4839 600/310 |

(Continued)

FOREIGN PATENT DOCUMENTS

| | | | |
|---|---|---|---|
| EP | 1 875 863 A1 | 1/2008 |
| EP | 2 474 264 A1 | 7/2012 |

(Continued)

OTHER PUBLICATIONS

Tanaka, "Dermoscopy basics and melanocytic lesions (Part 2 of 2)", Hong Kong J. Dermatol. Venereol. (2013) 21, 181-187 (Year: 2013).*

(Continued)

*Primary Examiner* — Serkan Akar
*Assistant Examiner* — Aminah Asghar
(74) *Attorney, Agent, or Firm* — Wolf, Greenfield & Sacks, P.C.

(57) ABSTRACT

The present technology relates to an information processing apparatus, an information processing method, and a program through which it is possible to intuitively and visually recognize skin conditions.
An analysis result acquisition unit acquires a skin condition analysis result based on an epidermis image obtained by capturing skin epidermis. A display control unit displays an analysis result image of a predetermined display form based on a skin condition analysis result on a display unit. Therefore, it is possible to intuitively and visually recognize skin (Continued)

conditions. The present technology can be applied to, for example, an electronic device configured to display a skin analysis result.

16 Claims, 26 Drawing Sheets

(51) Int. Cl.
A61B 5/107 (2006.01)
G06T 7/49 (2017.01)
(52) U.S. Cl.
CPC .............. *G06T 7/49* (2017.01); *A61B 5/1079* (2013.01); *A61B 2576/02* (2013.01); *G06T 2207/30088* (2013.01)
(58) Field of Classification Search
CPC ............... G06T 7/0012; G06T 7/49; G06T 2207/30088; G16H 30/40
See application file for complete search history.

(56) References Cited

U.S. PATENT DOCUMENTS

| | | | |
|---|---|---|---|
| 2009/0043363 A1* | 2/2009 | Cotton | A61B 5/442 607/88 |
| 2009/0054744 A1 | 2/2009 | Kitamura et al. | |
| 2012/0065518 A1* | 3/2012 | Mangoubi | G06T 7/0012 600/473 |
| 2012/0095350 A1* | 4/2012 | Goldman | A61B 5/0071 600/473 |
| 2012/0157821 A1 | 6/2012 | Kitamura et al. | |
| 2012/0300996 A1* | 11/2012 | Nakamura | G06K 9/52 382/128 |
| 2012/0307032 A1* | 12/2012 | Gomi | A61B 5/0077 348/77 |
| 2013/0076858 A1* | 3/2013 | Moon | H04N 13/261 348/43 |
| 2013/0120393 A1* | 5/2013 | Winnemoeller | G06T 11/001 345/441 |
| 2014/0100442 A1* | 4/2014 | Begin | A61B 8/466 600/411 |
| 2014/0139656 A1* | 5/2014 | Jeanne | A61B 5/0077 348/77 |
| 2014/0236019 A1* | 8/2014 | Rah | A61B 5/0075 600/473 |
| 2015/0373264 A1* | 12/2015 | Anzue | H04N 5/23293 348/333.05 |
| 2016/0063312 A1* | 3/2016 | Hara | A61B 5/0077 382/103 |
| 2016/0210764 A1 | 7/2016 | Gomi et al. | |
| 2016/0300094 A1* | 10/2016 | Lu | G06K 9/00885 |
| 2018/0263551 A1 | 9/2018 | Kimura et al. | |

FOREIGN PATENT DOCUMENTS

| | | |
|---|---|---|
| JP | 08-308634 A | 11/1996 |
| JP | 2006-305184 A | 11/2006 |
| JP | 2012-239768 A | 12/2012 |
| JP | 2013-169291 A | 9/2013 |
| WO | WO 2014/027522 A1 | 2/2014 |

OTHER PUBLICATIONS

International Search Report and Written Opinion and English translation thereof dated Jul. 14, 2015 in connection with International Application No. PCT/JP2015/060925.

International Preliminary Report on Patentability and English translation thereof dated Oct. 27, 2016 in connection with International Application No. PCT/JP2015/060925.

* cited by examiner

FIG. 1
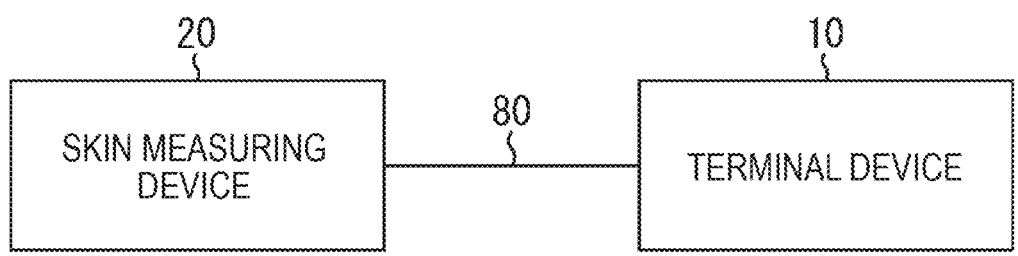
1

INFORMATION PROCESSING APPARATUS, INFORMATION PROCESSING METHOD, AND NON-TRANSITORY COMPUTER-READABLE MEDIUM FOR ACQUIRING AND DISPLAYING A SKIN CONDITION ANALYSIS RESULT BASED ON AN EPIDERMIS IMAGE

CROSS-REFERENCE TO RELATED APPLICATIONS

This application claims the benefit under 35 U.S.C. § 371 as a U.S. National Stage Entry of International Application No. PCT/JP2015/060925, filed in the Japanese Patent Office as a Receiving Office on Apr. 8, 2015, which claims priority to Japanese Patent Application Number JP 2014-086916, filed in the Japanese Patent Office on Apr. 18, 2014, each of which is hereby incorporated by reference in its entirety.

TECHNICAL FIELD

The present technology relates to an information processing apparatus, an information processing method, and a program, and particularly, to an information processing apparatus, an information processing method, and a program through which it is possible to intuitively and visually recognize skin conditions.

BACKGROUND ART

In the related art, technology in which a skin image obtained by capturing human skin is analyzed and skin texture conditions are evaluated is proposed (for example, refer to Patent Literature 1).

CITATION LIST

Patent Literature

Patent Literature 1: JP 2012-239768A

SUMMARY OF INVENTION

Technical Problem

When the technology disclosed in Patent Literature 1 is used, it is possible to evaluate skin texture conditions. However, there are demands to intuitively and visually recognize skin conditions.

The present technology has been made in view of the above-described circumstances and through which it is possible to intuitively and visually recognize skin conditions.

Solution to Problem

According to the present disclosure, there is provided an information processing apparatus including an acquisition unit configured to acquire a skin condition analysis result based on an epidermis image obtained by capturing skin epidermis, and a display control unit configured to display an analysis result image of a predetermined display form based on the skin condition analysis result on a display unit.

The display control unit may display the analysis result image of a display form in which cristae cutis blocks adjacent through sulci cutis are differently expressed according to a surface area of cristae cutis.

The display control unit may perform display such that the cristae cutis blocks are expressed in different colors of a same color family with different shades.

The display control unit may perform display such that a width of the sulcus cutis is indicated by a type of a line, and a depth of the sulcus cutis is indicated by a color shade.

The display control unit may perform display such that other skin conditions overlap the cristae cutis blocks that are expressed in different colors of a same color family with different shades.

The display control unit may perform display such that a distribution of pores further overlaps the cristae cutis blocks that are expressed in different colors of a same color family with different shades.

The distribution of the pores may be a distribution of clogged pores and a simple clogged pore and an acne risk serving as a cause of acne may be expressed in different colors.

The display control unit may display the analysis result image of a display form in which cristae cutis blocks having a specific shape are differently expressed according to a shape of cristae cutis.

The display control unit may display the analysis result image of a display form in which a gradation is applied according to directionality of texture by cristae cutis.

The display control unit may display the analysis result image of a display form in which a color or a symbol is applied according to directionality of texture by sulci cutis.

The display control unit may display the analysis result image of a display form according to cross sections of sulci cutis and cristae cutis.

The display control unit may display the analysis result image of a display form in which at least one of a clogged pore distribution, a pore opening distribution, and a comedo distribution is expressed in a plurality of levels with shades of a same color family.

In the clogged pore distribution, a simple clogged pore and an acne risk serving as a cause of acne may be expressed in different colors.

When a user captures skin epidermis of a face, the display control unit may display information indicating a measurement optimal region that is a region suitable as a target of a skin condition analysis process on a facial surface.

A recording unit may further be included which is configured to perform matching of the measurement optimal region included in the epidermis image using a skin texture distribution obtained from the skin condition analysis result whenever the user captures the skin epidermis of a face, and record the epidermis image including at least the measurement optimal region in time series.

The recording unit may record the epidermis image according to settings performed by the user.

When the user captures the skin epidermis of a face, if a current imaging position is outside of an optimal imaging position, the display control unit may display a message for showing the optimal imaging position from the current imaging position.

When the user captures the skin epidermis of a face, if the current imaging position is outside of the optimal imaging position, the display control unit may display a distance from the current imaging position to the optimal imaging position.

The information processing apparatus may be an independent device or an internal block configuring one device.

An information processing method and a program according to an embodiment of the present technology is an information processing method and a program corresponding to the information processing apparatus according to an embodiment of the present technology described above.

In an information processing apparatus, an information processing method, and a program according to an aspect of the present disclosure, a skin condition analysis result based on an epidermis image obtained by capturing skin epidermis is acquired, and an analysis result image of a predetermined display form is displayed on a display unit on the basis of the skin condition analysis result.

Advantageous Effects of Invention

According to an aspect of the present technology, it is possible to intuitively and visually recognize skin conditions.

The effect described herein is not necessarily limited and may include any effect described in the present disclosure.

BRIEF DESCRIPTION OF DRAWINGS

FIG. 1 is a diagram showing a configuration of an embodiment of a skin analysis display system to which the present technology is applied.

FIG. 7 is a diagram showing analysis result images of display forms according to a shape of the cristae cutis.

FIG. 17 is a diagram showing a display example of an application.

FIG. 18 is a diagram showing a display example of an application.

DESCRIPTION OF EMBODIMENT(S)

Figure 2:
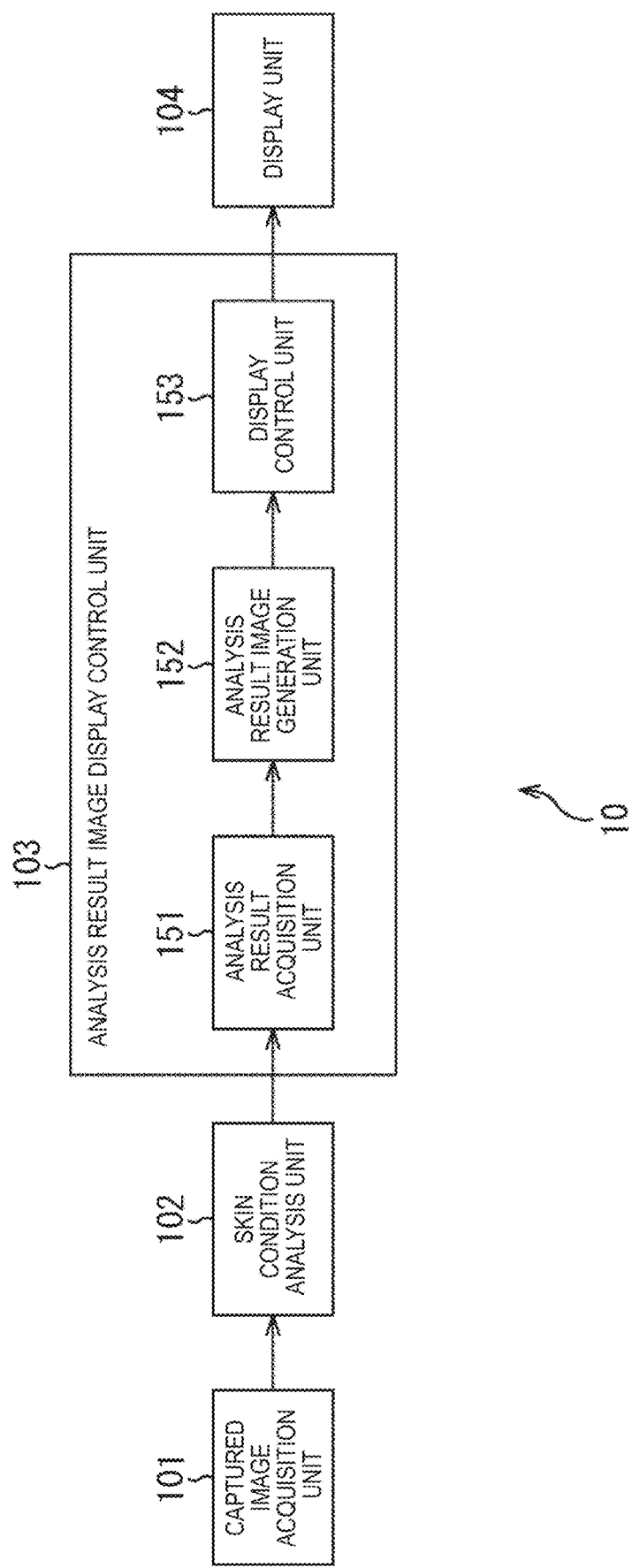
FIG. 2 is a diagram showing a functional configuration example of a terminal device.

Hereinafter, embodiments of the present technology will be described with reference to the appended drawings. The description will proceed in the following order.
1. System configuration
2. Flow of skin analysis display process
3. Display examples of analysis result images
4. Application example: representation of UI indicating measurement optimal region
5. Modification example: simplified display form
6. Other system configurations
7. Configuration of computer <1. System Configuration>
(Configuration of Skin Analysis Display System)

FIG. 1 is a diagram showing a configuration of an embodiment of a skin analysis display system to which the present technology is applied.

A skin analysis display system 1 of FIG. 1 presents, to a user, information about an image (hereinafter referred to as an "analysis result image") of a predetermined display form according to an analysis result of skin conditions of the user. As shown in FIG. 1, the skin analysis display system 1 includes a terminal device 10 and a skin measuring device 20.

The terminal device 10 is an electronic device, for example, a dedicated skin analyzer, a personal computer, a mobile communication terminal such as a smartphone, and a tablet type portable information device. The skin measuring device 20 is connected to the terminal device 10 through a cable 80 that supports a predetermined standard. The skin measuring device 20 includes an imaging device therein. The skin measuring device 20 captures (measures) the skin epidermis of the user's face, and provides a captured image obtained as the result (hereinafter referred to as an "epidermis image") to the terminal device 10 through the cable 80.

Here, the skin measuring device 20 preferably includes a manual focus adjustment function, a light source capable of uniformly emitting illumination light toward an entire subject, and a macro lens through which it is possible to perform capturing to the extent that a structure of a skin surface can be recognized. In addition, the skin measuring device 20 preferably includes an attachment causing the front of a lens to come in close contact with skin such that a focus position is fixed and capturing is performed each time. In this case, in order to prevent an influence of external light, a light blocking function may be provided in the attachment. The terminal device 10 and the skin measuring device 20 may be connected by a wire or may be connected through, for example, predetermined wireless communication.

The captured image is provided to the terminal device 10 from the skin measuring device 20 through the cable 80. The terminal device 10 performs an analysis process in which skin conditions of the user are analyzed based on the captured image from the skin measuring device 20. In addition, the terminal device 10 generates an analysis result image based on the analysis result of skin conditions and displays the image on a display unit.

(Configuration of Terminal Device)

FIG. 2 is a diagram showing a functional configuration example of the terminal device 10 of FIG. 1.

As shown in FIG. 2, the terminal device 10 includes a captured image acquisition unit 101, a skin condition analysis unit 102, an analysis result image display control unit 103, and a display unit 104.

The captured image acquisition unit 101 acquires the captured image obtained by capturing the skin epidermis of the user's face that is provided from the skin measuring device 20, and provides the image to the skin condition analysis unit 102.

The skin condition analysis unit 102 performs an analysis process in which skin conditions of the user are analyzed based on the captured image provided from the captured image acquisition unit 101. As the analysis process, for example, in the captured image obtained by capturing the skin epidermis of the user's face, an epidermis pattern within the epidermis image formed in the epidermis according to cristae cutis or sulci cutis is detected, and a congenital factor and an acquired factor among factors indicating skin texture conditions are analyzed based on the detection result and the epidermis image. Then, skin texture conditions of the user are evaluated based on the analysis result of the congenital factor and the acquired factor.

As a skin condition analysis result, for example, information about a surface area and a shape of cristae cutis, directionality of texture, a depth of sulci cutis, and cross sections of the sulci cutis and the cristae cutis is obtained. In addition, as the analysis process, for example, an analysis process of melanin and redness and an analysis process of a distribution of pores and comedos are performed, and analysis results of the processes may be obtained. The skin condition analysis result obtained in this manner is provided to the analysis result image display control unit 103.

Details of the analysis process are described in, for example, Patent Literature 1 proposed by the applicant.

The analysis result image display control unit 103 generates an analysis result image based on the skin condition analysis result obtained by the skin condition analysis unit 102 and displays the image on the display unit 104 including a liquid crystal display (LCD) or the like. The display unit 104 is not limited to the liquid crystal display, and the image may be directly displayed on a facial surface of the user through, for example, a projector. The analysis result image display control unit 103 includes an analysis result acquisition unit 151, an analysis result image generation unit 152, and a display control unit 153.

The analysis result acquisition unit 151 acquires the skin condition analysis result provided from the skin condition analysis unit 102 and provides the result to the analysis result image generation unit 152. The analysis result image generation unit 152 generates an analysis result image of a predetermined display form according to the analysis result based on the skin condition analysis result provided from the analysis result acquisition unit 151, and provides the image to the display control unit 153. The display control unit 153 displays the analysis result image provided from the analysis result image generation unit 152 on the display unit 104. In addition, the display control unit 153 displays various pieces of information, for example, a message, on the display unit 104.

<2. Flow of Skin Analysis Display Process>

(Flow of Skin Analysis Display Process)

Next, a flow of a skin analysis display process performed by the terminal device 10 of FIG. 1 will be described with reference to a flowchart of FIG. 3.

In Step S101, the captured image acquisition unit 101 acquires the captured image provided from the skin measuring device 20 and provides the image to the skin condition analysis unit 102.

In Step S102, the skin condition analysis unit 102 performs an analysis process in which skin conditions of the user are analyzed based on the captured image provided from the captured image acquisition unit 101. In the analysis process, for example, an epidermis pattern within the epidermis image is detected and at least one of an acquired factor and a congenital factor is analyzed based on the detection result and the epidermis image, and further skin conditions of the user are evaluated based on the analysis result.

In Step S103, the analysis result image display control unit 103 performs an analysis result image display control process based on the skin condition analysis result provided from the skin condition analysis unit 102. In the analysis result image display control process, an analysis result image based on the skin condition analysis result obtained by the skin condition analysis unit 102 is displayed on the display unit 104. Details of the analysis result image display control process will be described below with reference to a flowchart of FIG. 4. When the process of Step S103 ends, the skin analysis display process ends.

The skin analysis display process has been described above. In the skin analysis display process, an image of the skin epidermis of the user's face captured by the skin measuring device 20 is analyzed, an analysis result image of a predetermined display form according to the analysis result is generated, and the image is displayed on the display unit 104.

(Flow of Analysis Result Image Display Control Process)

Next, details of an analysis result image display control process corresponding to Step S103 of FIG. 3 will be described with reference to a flowchart of FIG. 4.

In Step S151, the analysis result acquisition unit 151 acquires the skin condition analysis result obtained by the skin condition analysis unit 102 and provides the result to the analysis result image generation unit 152.

In Step S152, the analysis result image generation unit 152 generates an analysis result image based on the skin condition analysis result provided from the analysis result acquisition unit 151, and provides the image to the display control unit 153.

In Step S153, the display control unit 153 displays the analysis result image generated in the process of Step S152 on the display unit 104. When the process of Step S153 ends, the process returns to Step S103 of FIG. 3.

The analysis result image display control process has been described above. In the analysis result image display control process, an analysis result image of a predetermined display form according to the analysis result of the image of the skin epidermis of the user's face is generated, and the analysis result image is displayed on the display unit 104. Therefore, information obtained from the skin analysis result, for example, fineness of texture and whether the skin is in good condition, is represented according to a predetermined display form (a user interface (UI)), and thus the user can intuitively and visually recognize his or her skin conditions.

<3. Display Examples of Analysis Result Images>

Next, display examples of analysis result images displayed on the display unit 104 according to the analysis result image display control process of FIG. 4 will be described with reference to FIG. 5 to FIG. 18.

(1) Display Form According to Surface Area of Cristae Cutis

Figure 5:
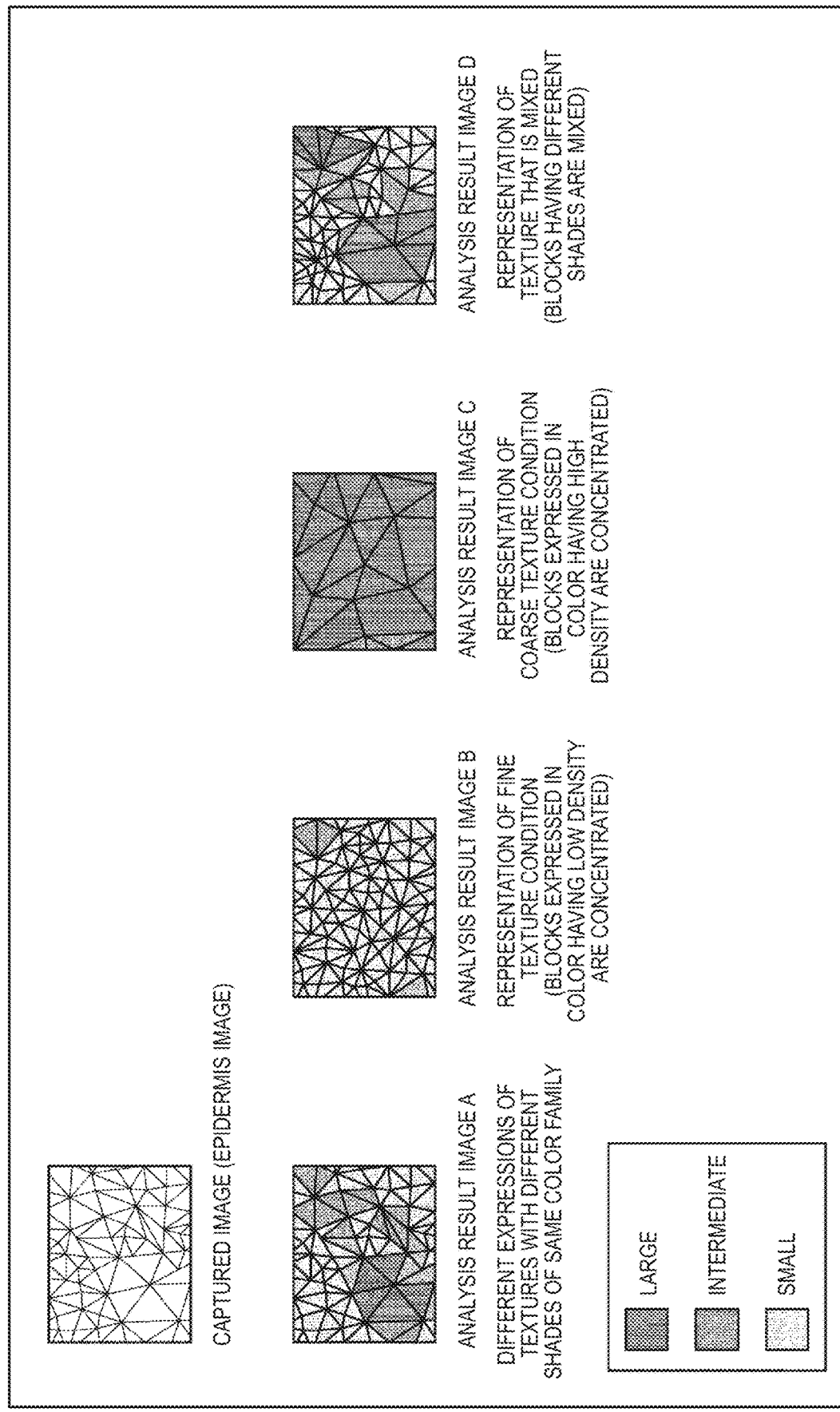
FIG. 5 is a diagram showing analysis result images of display forms according to a surface area of cristae cutis.

FIG. 5 is a diagram showing analysis result images of display forms according to a surface area of the cristae cutis. In FIG. 5, a captured image and analysis result images A to D obtained from the captured image are shown. In the analysis result images A to D, a surface area of the cristae cutis obtained by detecting an epidermis pattern within the epidermis image is compared with a predetermined threshold value, and cristae cutis blocks adjacent through the sulci cutis are expressed in a different color from the same color family with a different shade. Specifically, when the surface area of the cristae cutis is compared with the predetermined threshold value, the block of the cristae cutis is classified into three levels according to the surface area, and each level block is expressed in a different color, for example, dark green, light green, or green having an intermediate intensity.

For example, among the cristae cutis blocks of the analysis result image A, a block having a large surface area is expressed in a color having a high density, a block having an intermediate size is expressed in a different color having an intermediate density, and a block having a small size is expressed in a color having a low density. That is, a portion in which blocks expressed in a color having a low density are concentrated indicates that texture is fine. On the other hand, a portion in which blocks expressed in a color having a high density are concentrated indicates that texture is coarse. Therefore, it is possible to intuitively and visually recognize skin texture conditions according to the shade of the color.

In general, while such three patterns of the cristae cutis are mixed somewhat in the skin of an ordinary human, in the scope of a certain effective measurement region, when the proportion of the color having a low density is greater than colors having other densities, it indicates that texture is fine and the skin is in good condition. For example, in the analysis result image B, since blocks expressed in a color having a low density are concentrated and the proportion of such blocks is high, it indicates that texture is fine.

On the other hand, when the proportion of the color having a high density is greater than colors having other densities, it indicates that texture is coarse. For example, in the analysis result image C, since blocks expressed in a color having a high density are concentrated and the proportion of such blocks is high, it indicates that texture is coarse. Further, when colors with a different shade are mixed, it indicates that texture is mixed. For example, the analysis result image D shows that blocks expressed in colors having a different shade are mixed and texture is mixed.

That is, when the analysis result images B to D are compared, in general, the analysis result image B shows the most ideal texture condition, the analysis result image C shows the next best texture condition, and the analysis result image D shows a bad texture condition. Since epidermis blocks are expressed in colors having a different shade, it is possible to visually recognize, for example, a shape of texture and a distribution of sizes, at the same time, and it is possible to visually recognize fineness and quality of texture at a glance.

Figure 6:
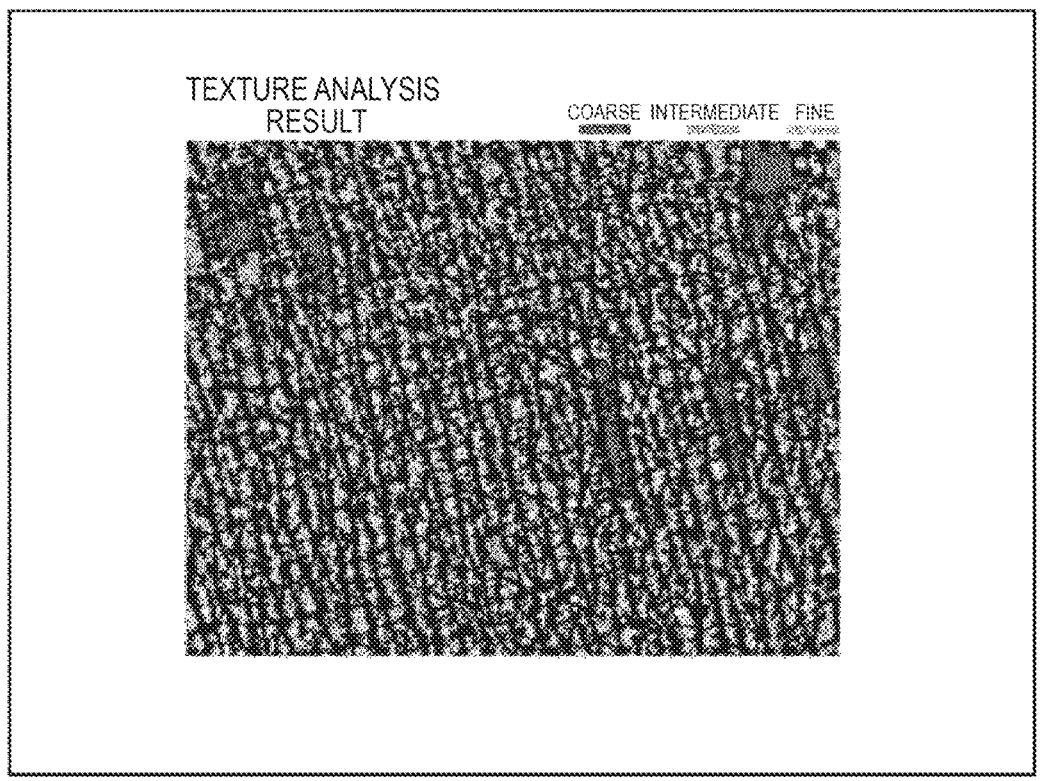
FIG. 6 is a diagram showing a display example of an analysis result image expressed by a display with a shade according to a surface area of the cristae cutis.

FIG. 6 shows a display example of an analysis result image expressed by a display with a shade according to a surface area of the cristae cutis. In FIG. 6, according to the surface area of the cristae cutis, the cristae cutis blocks are expressed at different densities of three levels, dark green, light green, and green having an intermediate intensity. However, since there are a great number of blocks expressed in light green in total, the skin is considered to have fine texture. By using such a display form, it is possible to intuitively and visually recognize skin texture conditions according to the shade of the color.

(2) Display Form According to Shape of Cristae Cutis

Figure 7:
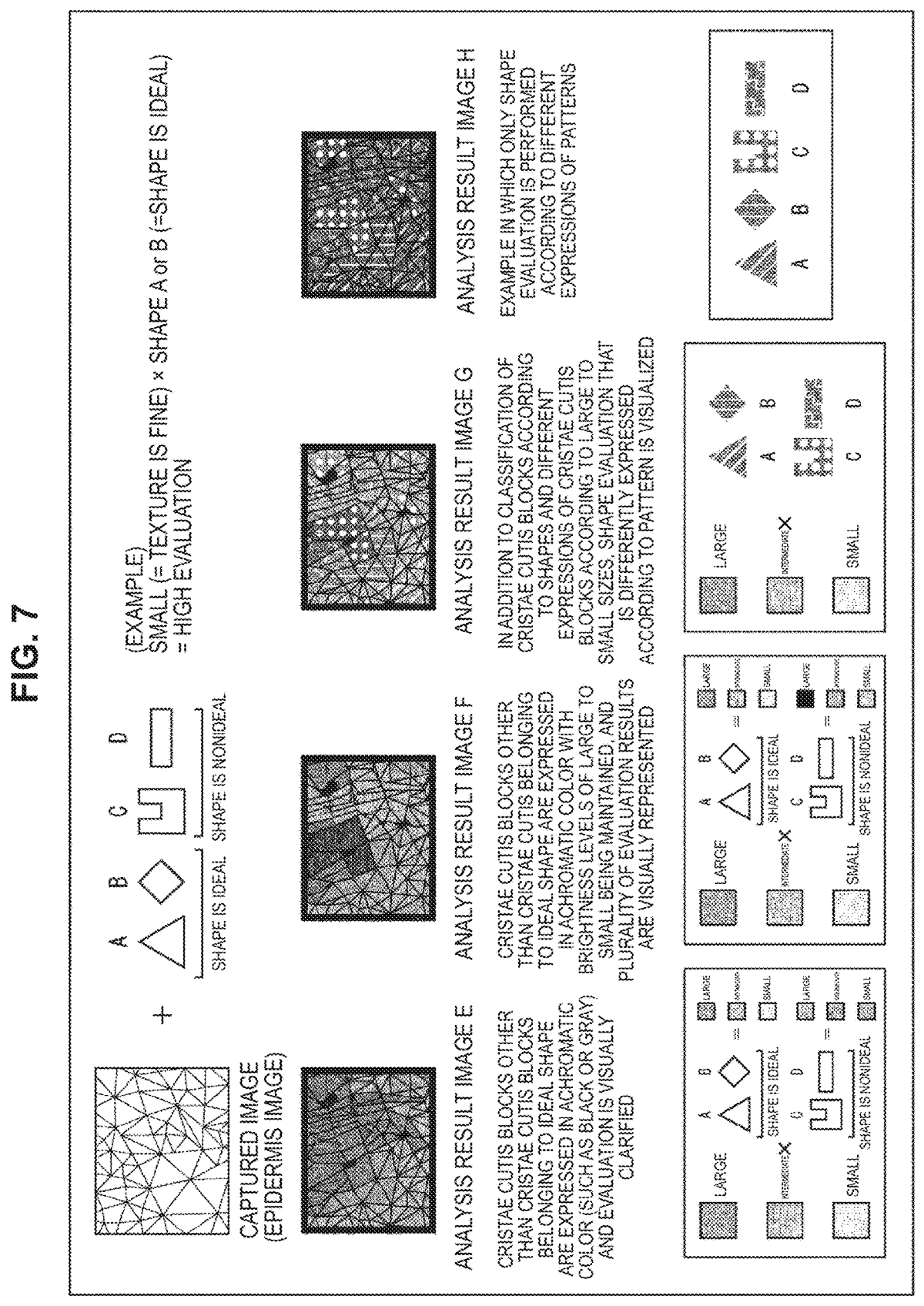

FIG. 7 is a diagram showing analysis result images of display forms according to a shape of the cristae cutis. In FIG. 7, reference shapes A to D for deciding relative merits of shapes of cristae cutis blocks are determined in advance. Here, among the reference shapes, the triangular shape A and the diamond shape B are ideal shapes, and the concave shape C and the rectangular shape D are nonideal shapes. Therefore, for example, when the cristae cutis block has a small surface area and is formed in the shape A or the shape B, it has a high evaluation value. The shapes A to D are examples of the reference shape, and other shapes are used as references that can be classified into an ideal shape and a nonideal shape. In addition, while an example in which the shapes are classified into two levels, an ideal shape and a nonideal shape, has been described here, the shapes may be classified into three or more levels.

In FIG. 7, analysis result images E to H obtained from the captured image are shown. In the analysis result images E and F, a surface area of the cristae cutis obtained by detecting an epidermis pattern within the epidermis image is compared with a predetermined threshold value, and the cristae cutis block is classified into three levels according to the surface area. In addition, in the analysis result images E and F, a shape of the cristae cutis block is compared with the reference shapes A to D, and it is determined whether the shape of the cristae cutis block is an ideal shape or a nonideal shape.

In the analysis result image E, among the cristae cutis blocks having an ideal shape, a block having a large surface area is expressed in a color having a high density, a block having an intermediate size is expressed in a color having an intermediate density, and a block having a small size is expressed in a color having a low density. Blocks whose shapes are nonideal are expressed in a single achromatic color, for example, black or gray. By using such a display form, cristae cutis blocks other than the cristae cutis blocks belonging to ideal shapes such as a triangle and a diamond shape, that is, cristae cutis blocks belonging to nonideal shapes such as a concave shape and a rectangular shape are expressed in an achromatic color. Therefore, evaluation using shapes is visually clarified and it is possible to intuitively and visually recognize skin texture conditions.

In the analysis result image F, cristae cutis blocks whose shapes are not ideal are also expressed with a shade of three levels according to the surface area. However, colors thereof are different from colors of the cristae cutis blocks having an ideal shape. For example, when a size of a cristae cutis block having an ideal shape is expressed in a green shade, a size of a cristae cutis block having a nonideal shape is expressed in a gray shade. By using such a display form, cristae cutis blocks other than the cristae cutis blocks belonging to ideal shapes such as a triangle and a diamond shape, that is, cristae cutis blocks belonging to nonideal shapes such as a concave shape and a rectangular shape are expressed in an achromatic color shade. Therefore, evaluation using a size and a shape of the surface area is visually clarified and it is possible to intuitively and visually recognize skin texture conditions.

A predetermined pattern is allocated to the reference shapes A to D, and a shape of the cristae cutis may be visually recognized by the pattern. For example, a right downward oblique line pattern can be allocated to the triangular shape A, a vertical stripe pattern can be allocated to the diamond shape B, a polka dot pattern can be allocated to the concave shape C, and a stepwise pattern can be allocated to the rectangular shape D.

In the analysis result image G, although different expression according to a shape of the cristae cutis block is not performed, a predetermined pattern is allocated to the reference shapes A to D. Therefore, the cristae cutis blocks are expressed with a shade of three levels according to the surface area, and different expression according to a pattern corresponding to the shape is performed. For example, a right downward oblique line pattern is allocated to the shape A, a vertical stripe pattern is allocated to the shape B, a polka dot pattern is allocated to the shape C, and a stepwise pattern is allocated to the shape D. Therefore, a pattern corresponding to the shape is provided to each epidermis block. Alternatively, without performing different expression according to the shape of the cristae cutis block, four colors may be differently expressed according to the shape of the cristae cutis block. By using such a display form, since each epidermis block is expressed in a green shade according to the surface area and a pattern corresponding to the shape is provided, evaluation using a size and a shape of the surface area is visually clarified, and it is possible to intuitively and visually recognize skin texture conditions.

In the analysis result image H, although different expression according to a surface area of the cristae cutis block is not performed, a predetermined pattern is allocated to the reference shapes A to D. Therefore, different expression according to a pattern corresponding to the shape is performed. For example, a right downward oblique line pattern is allocated to the shape A, a vertical stripe pattern is allocated to the shape B, a polka dot pattern is allocated to the shape C, and a stepwise pattern is allocated to the shape D. Therefore, a pattern corresponding to the shape is provided to each epidermis block. Alternatively, without performing different expression according to the shape of the cristae cutis block, four colors may be differently expressed according to the shape of the cristae cutis block. By using such a display form, since a pattern corresponding to the shape is provided to each epidermis block, evaluation using shapes is visually clarified and it is possible to intuitively and visually recognize skin texture conditions.

(3) Display Form According to Directionality of Texture by Cristae Cutis

Figure 8:
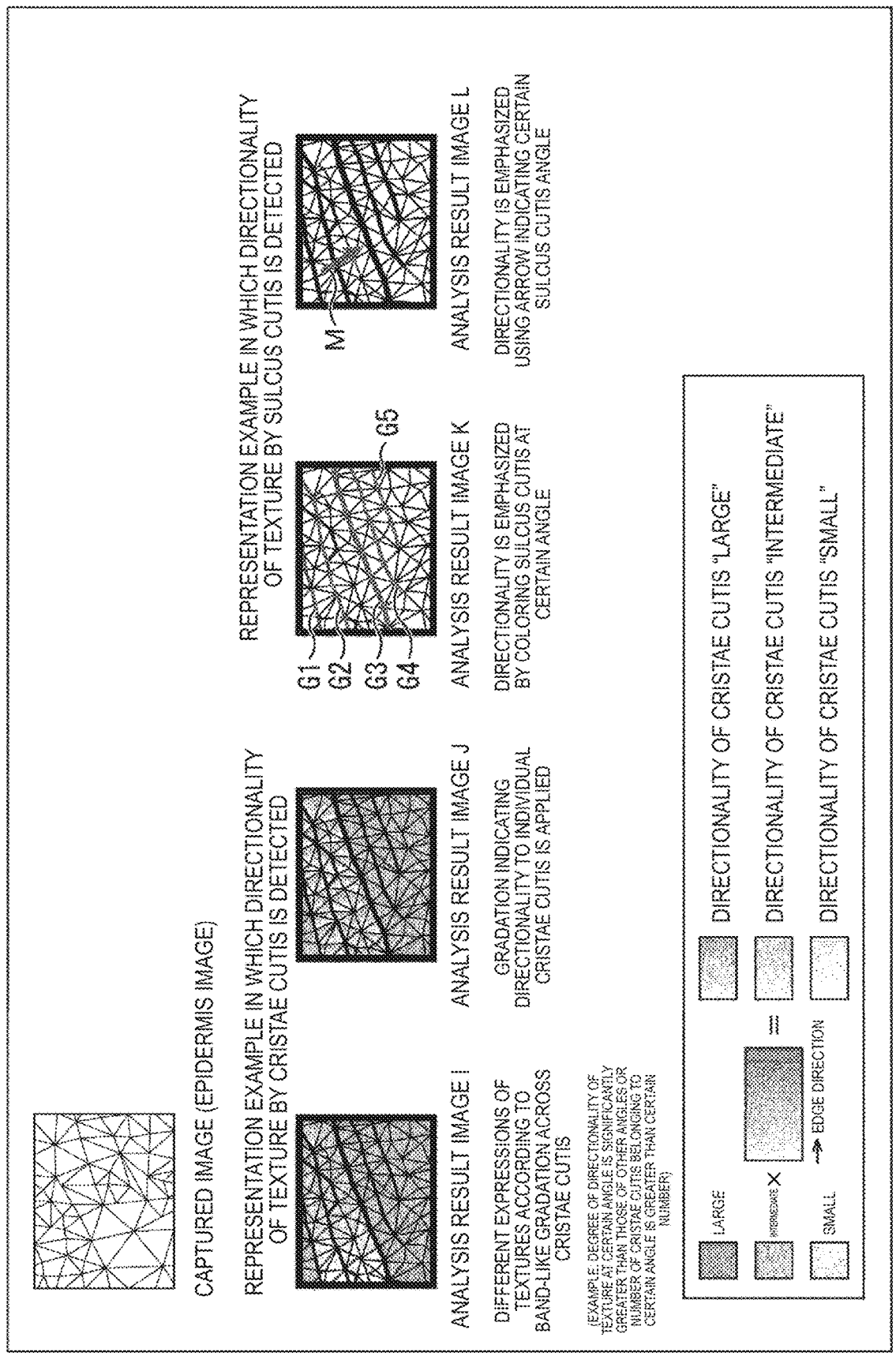
FIG. 8 is a diagram showing analysis result images of display forms according to directionality of texture by the cristae cutis.

FIG. 8 is a diagram showing analysis result images of display forms according to directionality of texture by the cristae cutis. In FIG. 8, the cristae cutis and the sulci cutis are differently expressed according to directionality of texture.

In FIG. 8, analysis result images I to L obtained from the captured image are shown. In the analysis result images I and J, colors are expressed at different densities of three levels according to the surface area of the cristae cutis obtained by detecting an epidermis pattern within the epidermis image. In addition, in the analysis result images I and J, a gradation according to directionality of texture by the cristae cutis is applied to colors expressed at different densities of three levels.

In the analysis result image I, when a color shade in a band-like region across a plurality of cristae cutis blocks is differently expressed according to the gradation, directionality of texture by the cristae cutis is represented. Here, for example, when a degree of directionality of texture at a certain angle is significantly greater than those of other angles, or when the number of cristae cutis belonging to a certain angle is greater than a certain number, a color shade in a band-like region is differently expressed according to the gradation such that the angle is expressed. In addition, in the analysis result image J, when a color shade in each cristae cutis block is differently expressed according to the gradation, directionality of texture by the cristae cutis is represented.

By using such a display form, according to the gradation, directionality of texture by the cristae cutis is clarified and it is possible to intuitively and visually recognize skin texture conditions.

In addition, in the analysis result images K and L, in particular, although the cristae cutis are not differently expressed, a color and a symbol are applied according to directionality of texture by the sulci cutis within the epidermis image.

In the analysis result image K, when sulci cutis G1 to G5 at a certain angle among sulci cutis within the epidermis image are colored, directionality of texture by the sulci cutis are displayed in an emphasized manner. Here, for example, when the sulci cutis G1 to G5 at a certain angle are colored in red that is different from colors of the other sulci cutis, it is possible to emphasize directionality of texture. In addition, in the analysis result image L, among sulci cutis within the epidermis image, an angle of a certain sulcus cutis is indicated by an arrow M and directionality of texture is displayed in an emphasized manner. In the analysis result image L, while directionality of texture by the sulcus cutis is indicated by the arrow M, the arrow M is an example and directionality of texture by the sulcus cutis may be emphasized by, for example, a symbol and a figure.

By using such a display form, directionality of texture by the sulcus cutis is clarified (emphasized) by a color and a symbol, and it is possible to intuitively and visually recognize skin texture conditions. Directionality of texture by the cristae cutis according to the gradation and directionality of texture by the sulcus cutis according to a color, a symbol or the like are used in combination, and these may be included in one analysis result image. In such a combination, directionality of texture is further clarified (emphasized).

(4) Display Forms According to Width and Depth of Sulci Cutis

Figure 9:
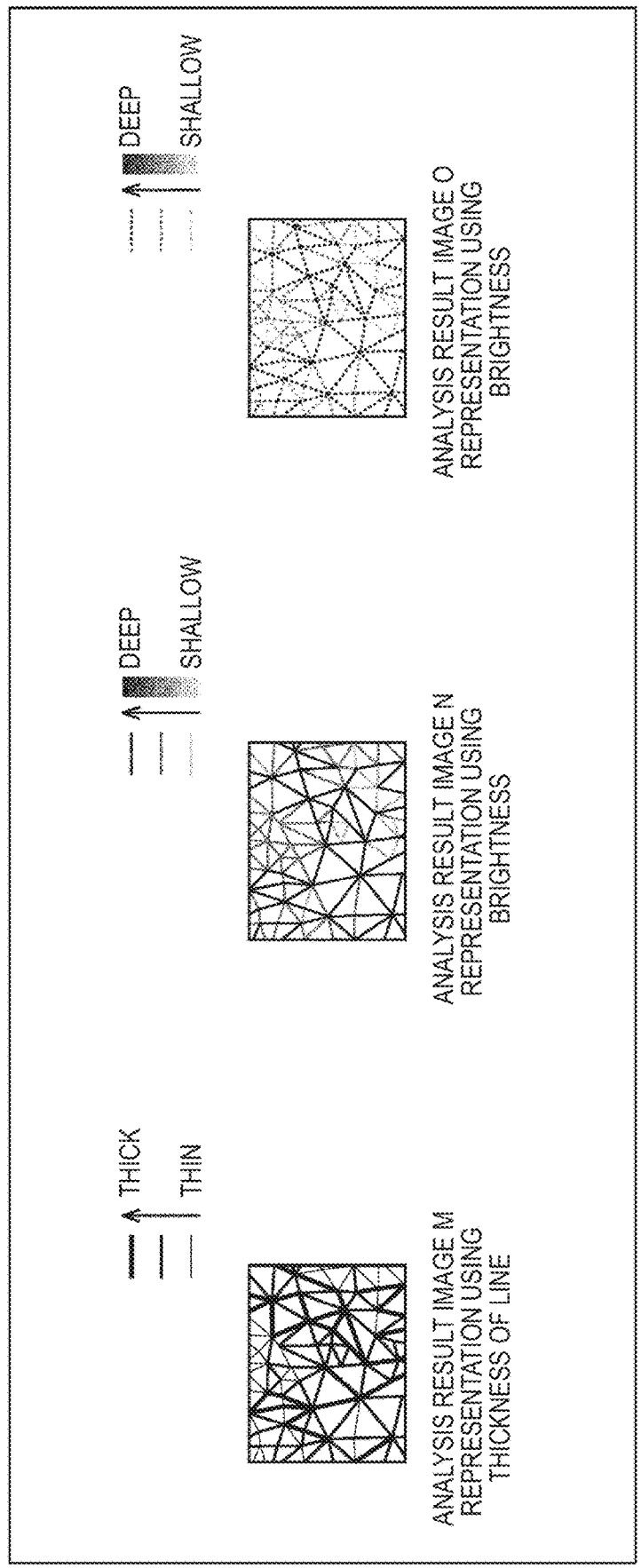
FIG. 9 is a diagram showing analysis result images of display forms according to a width and a depth of sulci cutis.

FIG. 9 is a diagram showing analysis result images of display forms according to a depth of the sulci cutis. In FIG. 9, analysis result images M to O are shown. In the analysis result image M, a width of the sulci cutis within the epidermis image is represented by a type of a line (a thickness of a line) indicating the sulci cutis. For example, in the analysis result image M, a thinner width of the line indicates a thinner width of the sulci cutis, and a thicker width of the line indicates a thicker width of the sulci cutis.

In the analysis result image N, a depth of the sulcus cutis within the epidermis image is indicated by a shade of a line indicating the sulcus cutis. For example, in the analysis result image N, a lighter shade of the line indicates a shallower depth of the sulcus cutis, and a darker shade of the line indicates a deeper depth of the sulcus cutis. In addition, in the analysis result image N, while a depth of the sulcus cutis is indicated by a shade of a black line, a color line such as a red line may be used instead of the black line. In the analysis result image O, a line indicating the sulcus cutis is expressed in a color, for example, red, and a depth of the sulcus cutis is expressed according to the shade of the color.

By using such a display form, a width and a depth of the sulci cutis are clarified and it is possible to intuitively and visually recognize skin conditions.

(5) Display Forms According to Cross Sections of Sulci Cutis and Cristae Cutis

Next, analysis result images of display forms according to cross sections of the sulci cutis and the cristae cutis will be described with reference to FIG. 10 to FIG. 12.

Figure 10:
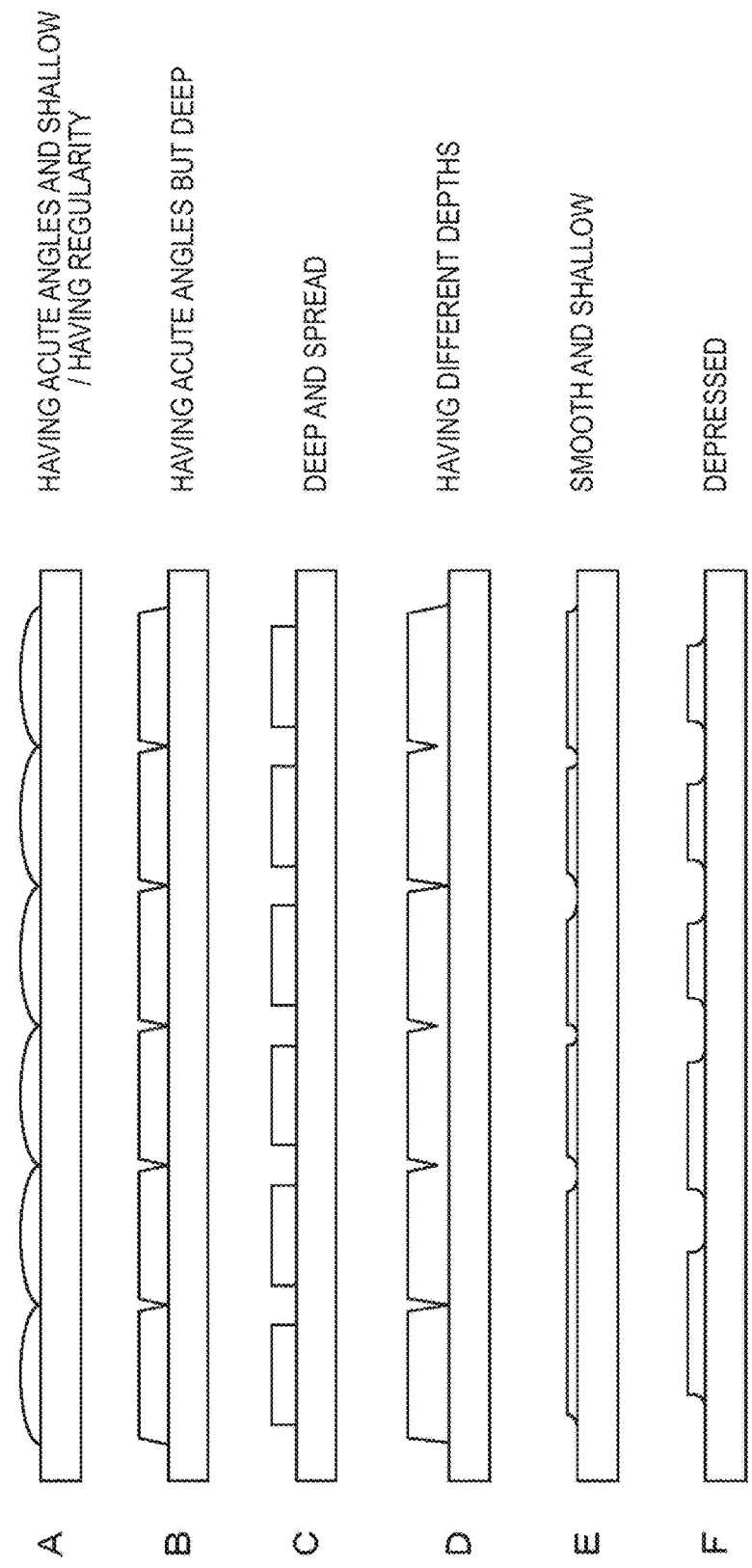
FIG. 10 is a diagram showing representation examples of cross sections of sulci cutis.

FIG. 10 is a diagram showing representation examples of cross sections of sulci cutis. FIG. 10 shows six representation examples of cross sections of sulci cutis. A in FIG. 10 shows cross sections that have acute angles, are shallow, and have regularity. B in FIG. 10 shows cross sections that have acute angles but are deep. C in FIG. 10 shows cross sections that are deep and spread. D in FIG. 10 shows cross sections that have different depths. E in FIG. 10 shows cross sections that are smooth and shallow. F in FIG. 10 shows cross sections that are depressed.

Figure 11:
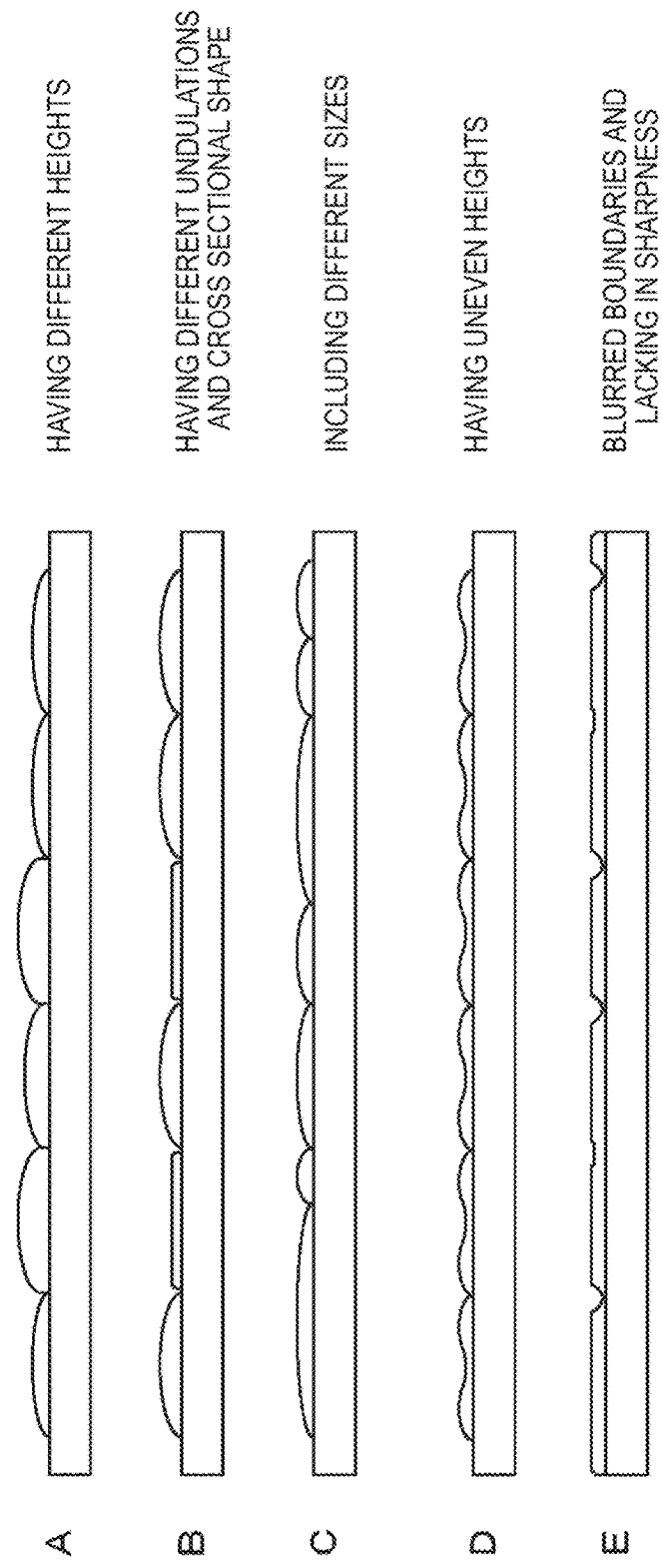
FIG. 11 is a diagram showing representation examples of cross sections of cristae cutis.

In addition, FIG. 11 is a diagram showing representation examples of cross sections of cristae cutis. FIG. 11 shows five representation examples of cross sections of cristae cutis. A in FIG. 11 shows cross sections having different heights. B in FIG. 11 shows cross sections having different undulations and cross sectional shapes. C in FIG. 11 shows cross sections having different sizes. D in FIG. 11 shows cross sections having uneven heights. E in FIG. 11 shows cross sections whose boundaries are blurred without sharpness.

Figure 12:
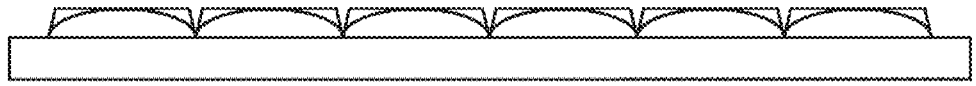
FIG. 12 is a diagram showing an analysis result image of a display form according to cross sections of the sulci cutis and the cristae cutis.

FIG. 12 shows an analysis result image P of a display form according to cross sections of the sulci cutis and the cristae cutis. By using such a display form, for example, elasticity of texture, comparison with previously measured texture conditions, comparison with ideal texture conditions and the like can be represented. In addition, it is easy to understand a relation between a depth or a size of a clogged pore and sulcus cutis conditions, a relation between an amount of moisture and sulcus cutis conditions, and a relation between melasma and cristae cutis conditions. In the analysis result image P of FIG. 12, while cross sections are two-dimensionally represented, other display forms may be used, for example, shapes including cross sections of the sulci cutis and the cristae cutis are three-dimensionally displayed. Further, in the skin condition analysis process performed in the skin condition analysis unit 102, since an analysis result of a congenital factor and an acquired factor is obtained, it is possible to correspond to both the epidermis and the dermis.

(6) Display Form According to Analysis Result of Melanin and Redness

Figure 13:
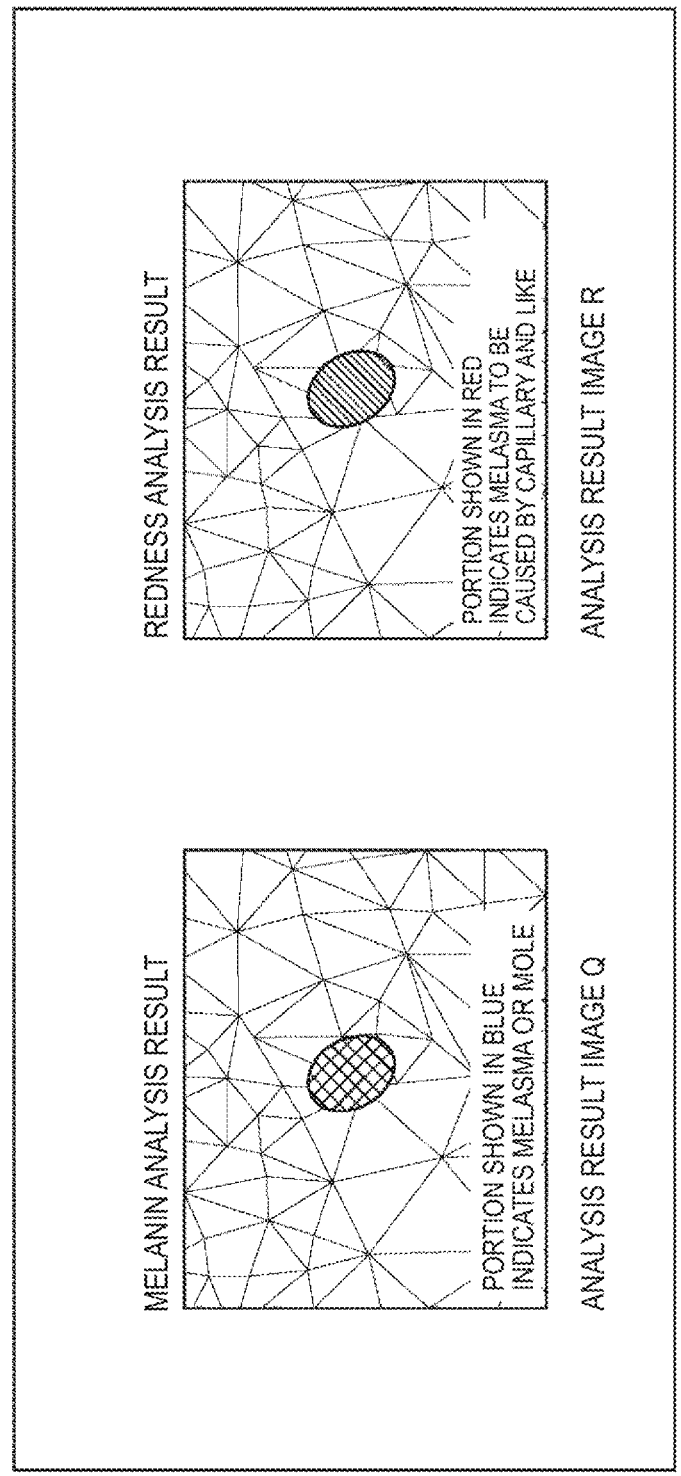
FIG. 13 is a diagram showing analysis result images of display forms according to an analysis result of melanin and redness.

FIG. 13 is a diagram showing analysis result images of display forms according to an analysis result of melanin and redness. In FIG. 13, in an analysis result image Q, according to an analysis result of melanin, a position (a hatched region in the drawing) of melasma or a mole is expressed in a color (for example, blue) indicating the presence thereof in the epidermis image. In addition, in an analysis result image R, according to an analysis result of redness, a position (a hatched region in the drawing) of melasma considered to be caused by a capillary and the like is expressed in a color (for example, red) indicating the presence thereof in the epidermis image.

By using such a display form, the position of the melasma or the mole is clarified in the epidermis image and it is possible to intuitively and visually recognize skin conditions.

(7) Display Form According to Distribution of Pores and Comedos

Figure 14:
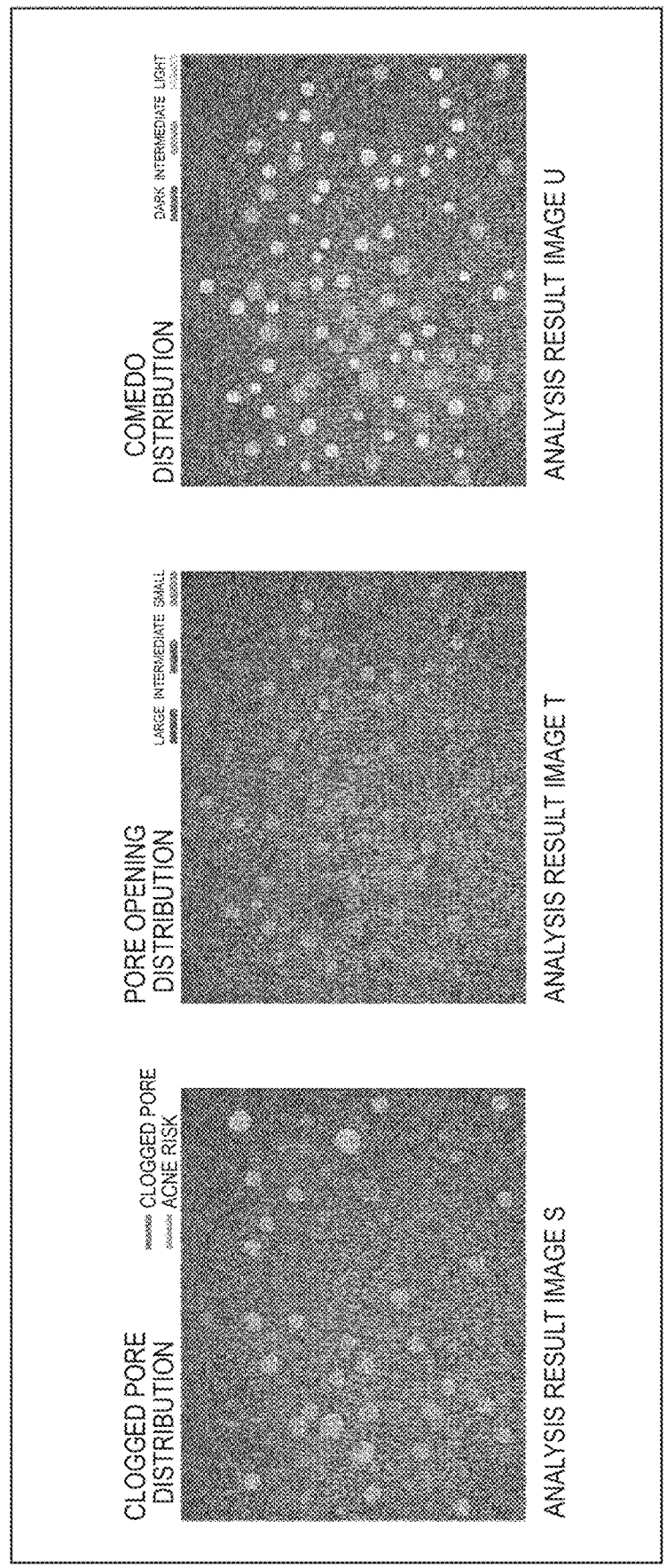
FIG. 14 is a diagram showing analysis result images of display forms according to a distribution of pores and comedos.

FIG. 14 is a diagram showing analysis result images of display forms according to a distribution of pores and comedos. In FIG. 14, in an analysis result image S, according to an analysis result of a distribution of clogged pores, positions of a "clogged pore" and an "acne risk" are expressed in a color indicating the presence thereof in the epidermis image. Here, the term "clogged pore" refers to conditions in which a pore is clogged with sebum, keratin plugs or the like. In addition, the term "acne risk" refers to conditions in which acne is caused.

When the "clogged pore" and the "acne risk" are expressed in different colors (for example, green and yellow) using such a display form, it is possible to intuitively and visually recognize whether the clogged pore is a simple clogged pore or there is an acne risk. In particular, when a color having noticeable color contrast, for example, yellow, is used for the "acne risk," it is possible to visually recognize the acne risk at a glance of which it is necessary to be informed with more attention.

In an analysis result image T, according to an analysis result of a distribution of pore openings, a position of the pore is expressed in a color (for example, purple) indicating the presence thereof in the epidermis image. A pore having a large opening is expressed in a color having a high density. A pore having an intermediate size is expressed in a color having an intermediate density. A pore having a small size is expressed in a color having a low density. By using such a display form, according to the shade of the color, it is possible to intuitively and visually recognize a size of an opening of the pore in addition to a distribution of pores.

In an analysis result image U, according to an analysis result of a distribution of comedos, a position of a comedo is expressed in a color (for example, pink) indicating the presence thereof in the epidermis image. A comedo having a high intensity is expressed in a color having a high density, a comedo having an intermediate intensity is expressed in a color having an intermediate density, and a comedo having a low intensity is expressed in a color having a low density. By using such a display form, according to the shade of the color, it is possible to intuitively and visually recognize an intensity of comedos in addition to a distribution of comedos.

(8) Display Form in which Skin Conditions Overlap Skin Texture Conditions

Next, an overlapping image of a display form in which skin conditions overlap skin texture conditions will be described with reference to FIG. 15 and FIG. 16.

Figure 15:
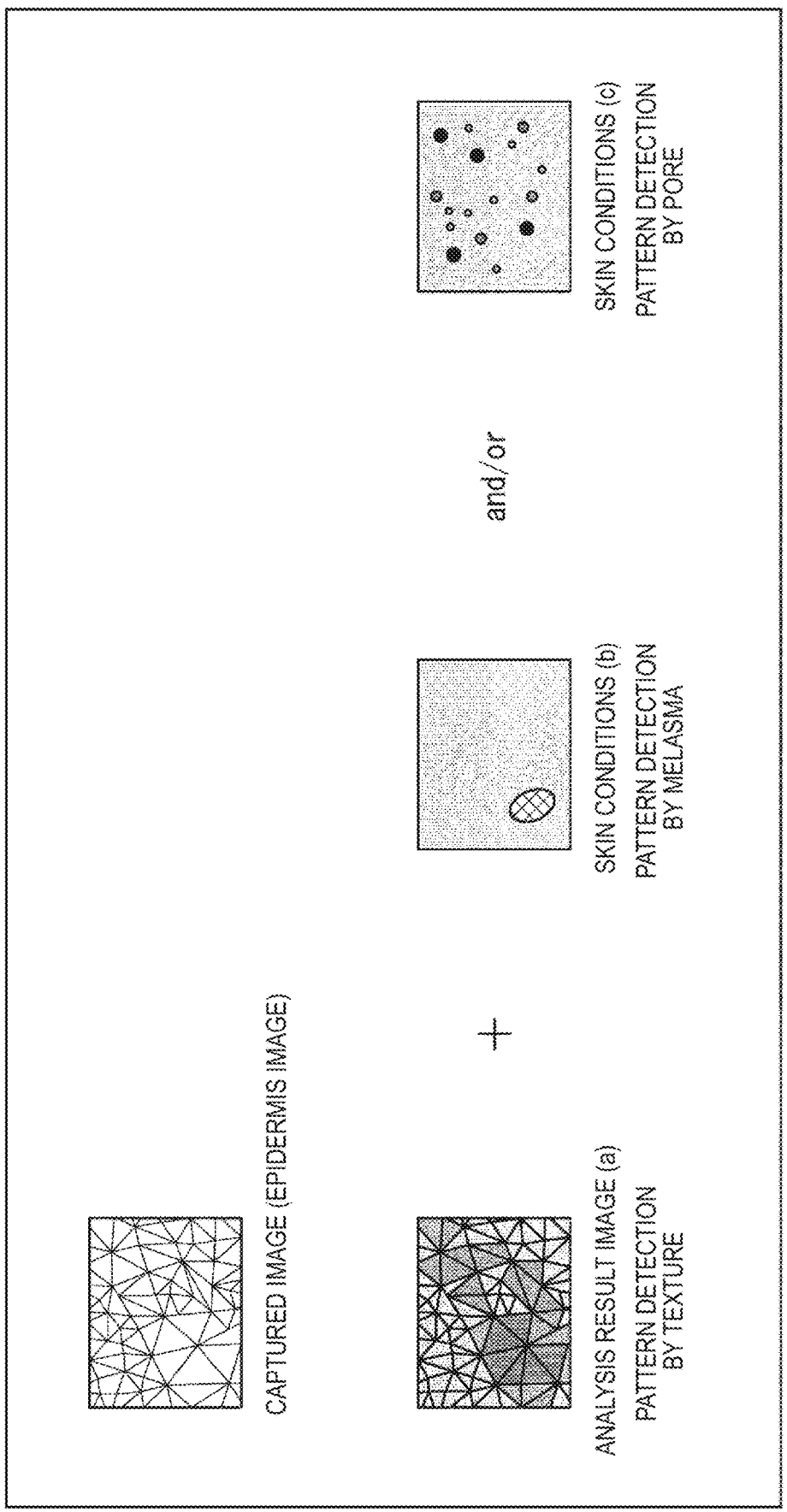
FIG. 15 is a diagram for describing an overlapping image.
Figure 16:
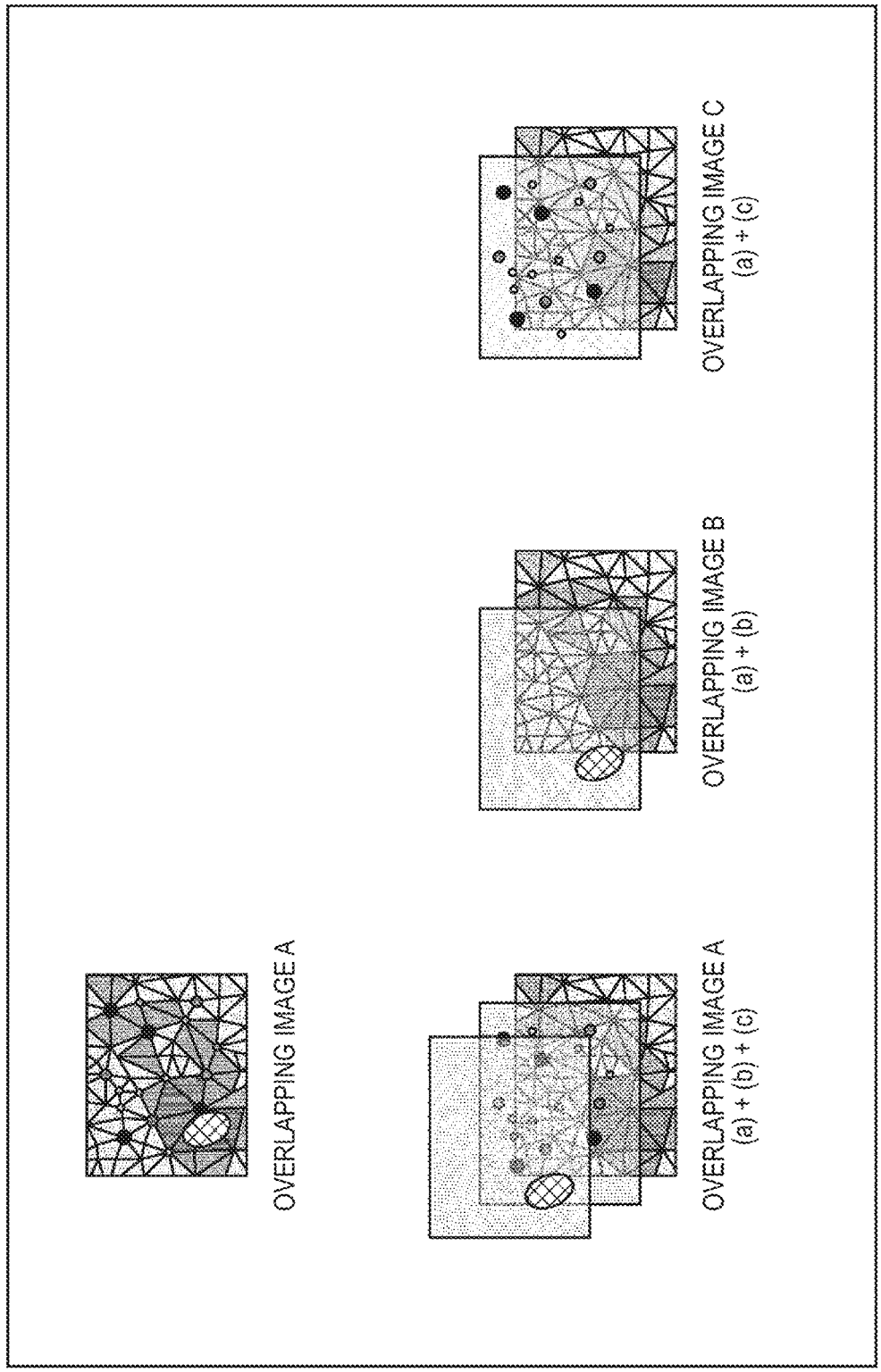
FIG. 16 is a diagram showing overlapping images of display forms in which skin conditions overlap skin texture conditions.

As shown in FIG. 15, at least one of skin conditions (b) of a display form according to an analysis result of melanin and redness and skin conditions (c) of a display form according to a distribution of pores and comedos can overlap an analysis result image (a) of a display form according to an analysis result of texture conditions. In such an overlapping manner, as shown in FIG. 16, an overlapping image A in which both the skin conditions (b) and the skin conditions (c) overlap the analysis result image (a), an overlapping image B in which only the skin conditions (b) overlap the analysis result image (a) and an overlapping image C in which only the skin conditions (c) overlap the analysis result image (a) are obtained.

Specifically, for example, at least one of the analysis result image Q (FIG. 13) of a display form according to an analysis result of melanin and redness and the analysis result image S (FIG. 14) of a display form according to an analysis result of a distribution of clogged pores can overlap the analysis result image A (FIG. 5) of a display form according to a surface area of the cristae cutis.

Here, as the texture conditions, instead of the analysis result image A (FIG. 5), other analysis result images, for example, the analysis result image E (FIG. 7) of a display form according to a shape of the cristae cutis and the analysis result image I (FIG. 8) of a display form according to directionality of texture by the cristae cutis can be used. In addition, as the skin conditions (b), instead of the analysis result image Q (FIG. 13), for example, the analysis result image R (FIG. 13) can be used. Further, as the skin conditions (c), instead of the analysis result image S (FIG. 14), for example, the analysis result image T (FIG. 14) or the analysis result image U (FIG. 14) can be used.

By using such a display form, since positions of melasma and moles and positions of pores and comedos are displayed in an overlapping manner with respect to texture conditions, it is possible to intuitively and visually recognize a relation between texture and melasma and moles and a relation between texture and pores and comedos. In addition, when a display form in which a color scheme that has a vivid color and a different color system is used is set for each texture condition and skin condition, even if such analysis result images overlap, it is possible to prevent colors from interfering with each other. Alternatively, without using the analysis result image (a), an overlapping image in which the skin conditions (b) and the skin conditions (c) overlap may be obtained.

(9) Display Example of Application

Next, a display example of an application that presents the above-described analysis result image and overlapping image will be described with reference to FIG. 17 and FIG. 18. The application is installed in the terminal device 10 in advance. Alternatively, the application is downloaded from an application server via the Internet and then installed.

Figure 17:
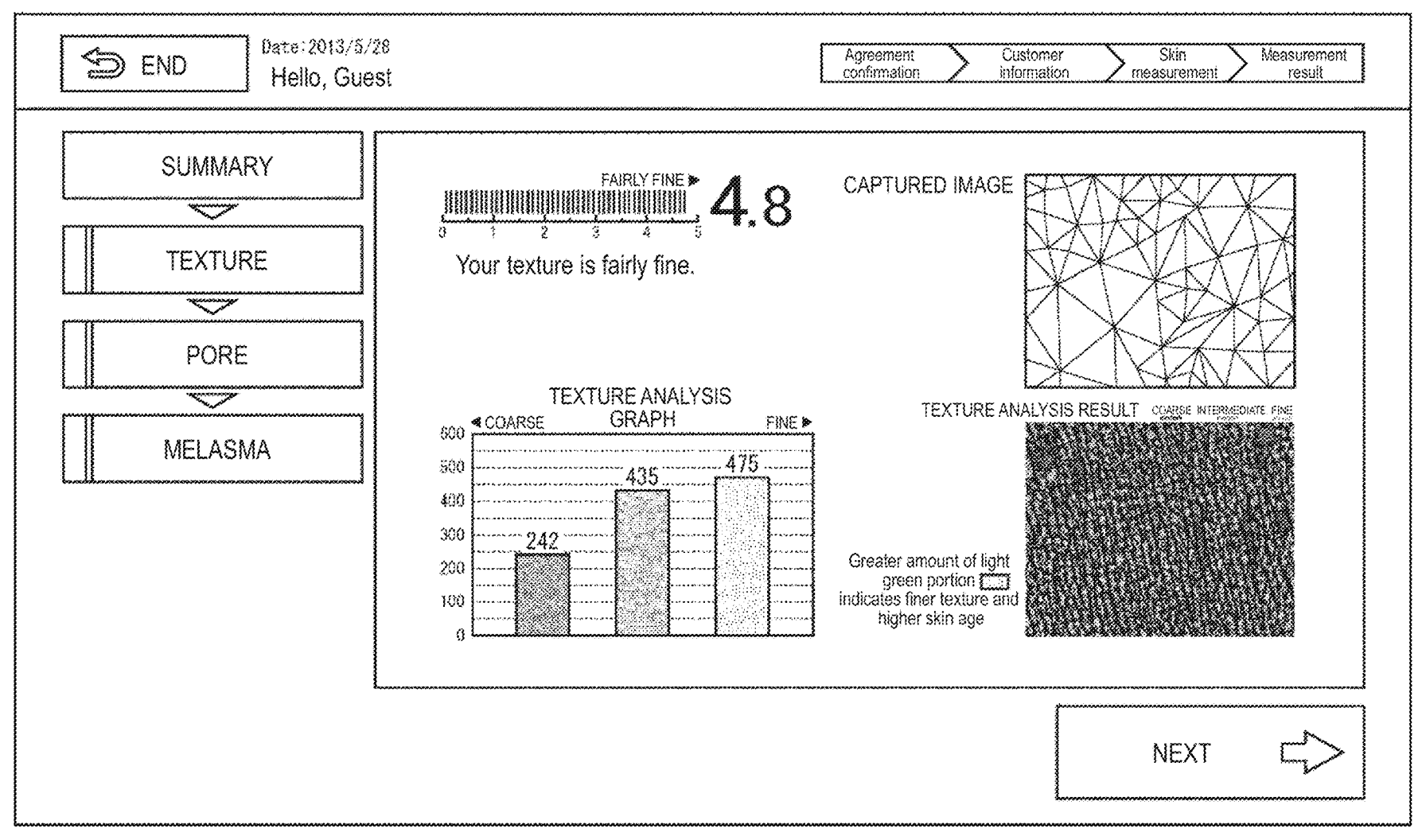
Figure 18:
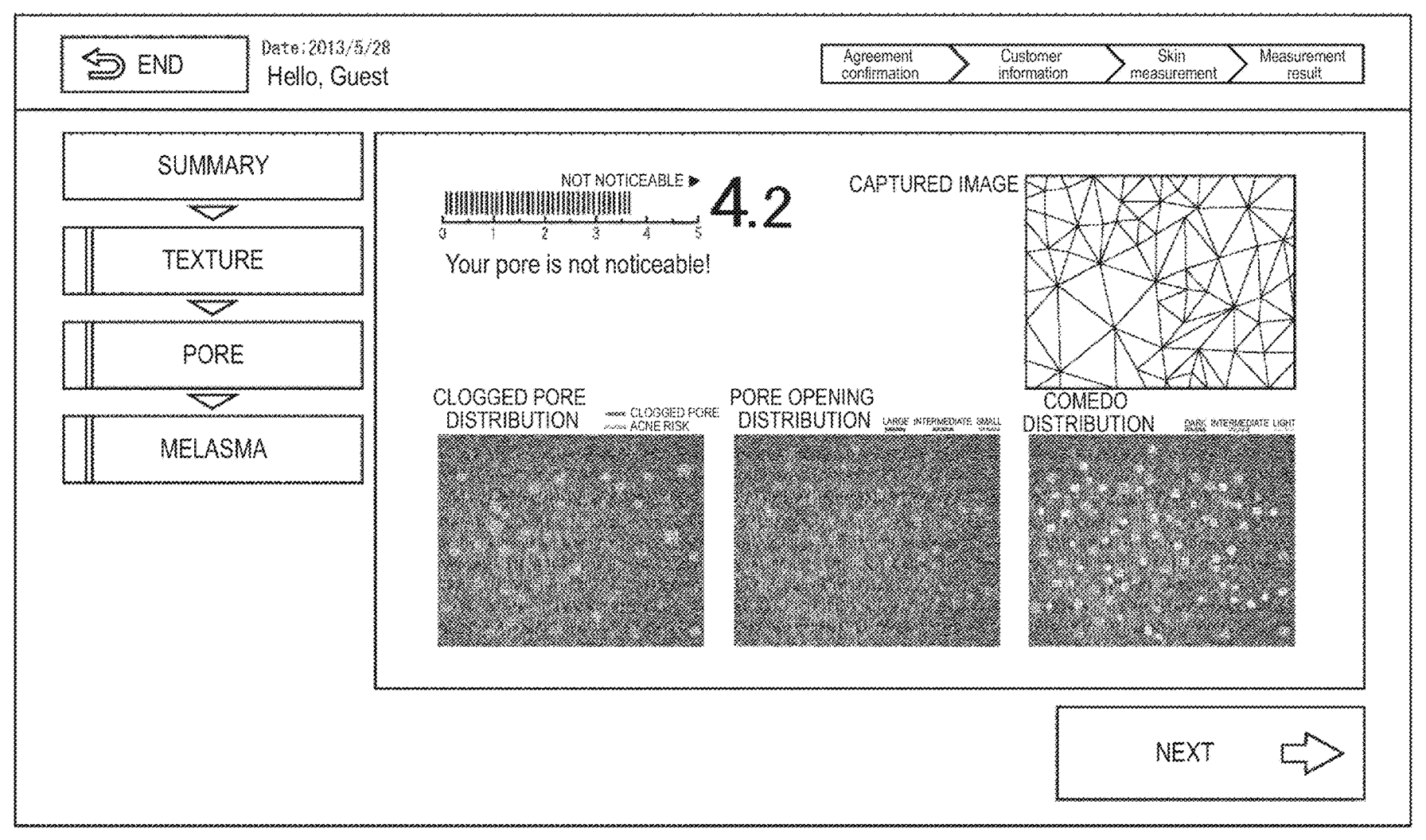

In FIG. 17, in addition to the analysis result image of a display form according to a surface area of the cristae cutis, a numeric value (for example, evaluation of texture) and a graph (for example, a texture analysis graph) obtained from the texture analysis result are displayed. In addition, in FIG. 18, in addition to the analysis result image of a display form according to a distribution of pores and comedos, a numeric value (for example, evaluation of pores) obtained from the analysis result of pores and comedos is displayed. Although not shown here, a screen of melasma is displayed in the same manner as a screen of the above-described texture and pore.

In this manner, when the analysis result image and the numeric value and the graph in connection with the analysis result image are displayed at the same time, the user can intuitively and visually recognize skin conditions and obtain relevant detailed information at the same time. As a result, the user confirms relevant detailed information and easily recognizes his or her skin conditions.

<4. Application Example: Representation of UI Indicating an Optimal Measurement Region>

Meanwhile, in the skin epidermis of the user's face, since there is a region (hereinafter referred to as a "measurement optimal region") that is suitable as a target of the analysis process, for example, a cheek, a mouth, or a forehead, in a region that is captured as an epidermis image serving as a target of the skin condition analysis process, the epidermis image obtained by capturing the measurement optimal region can be analyzed.

Figure 19:
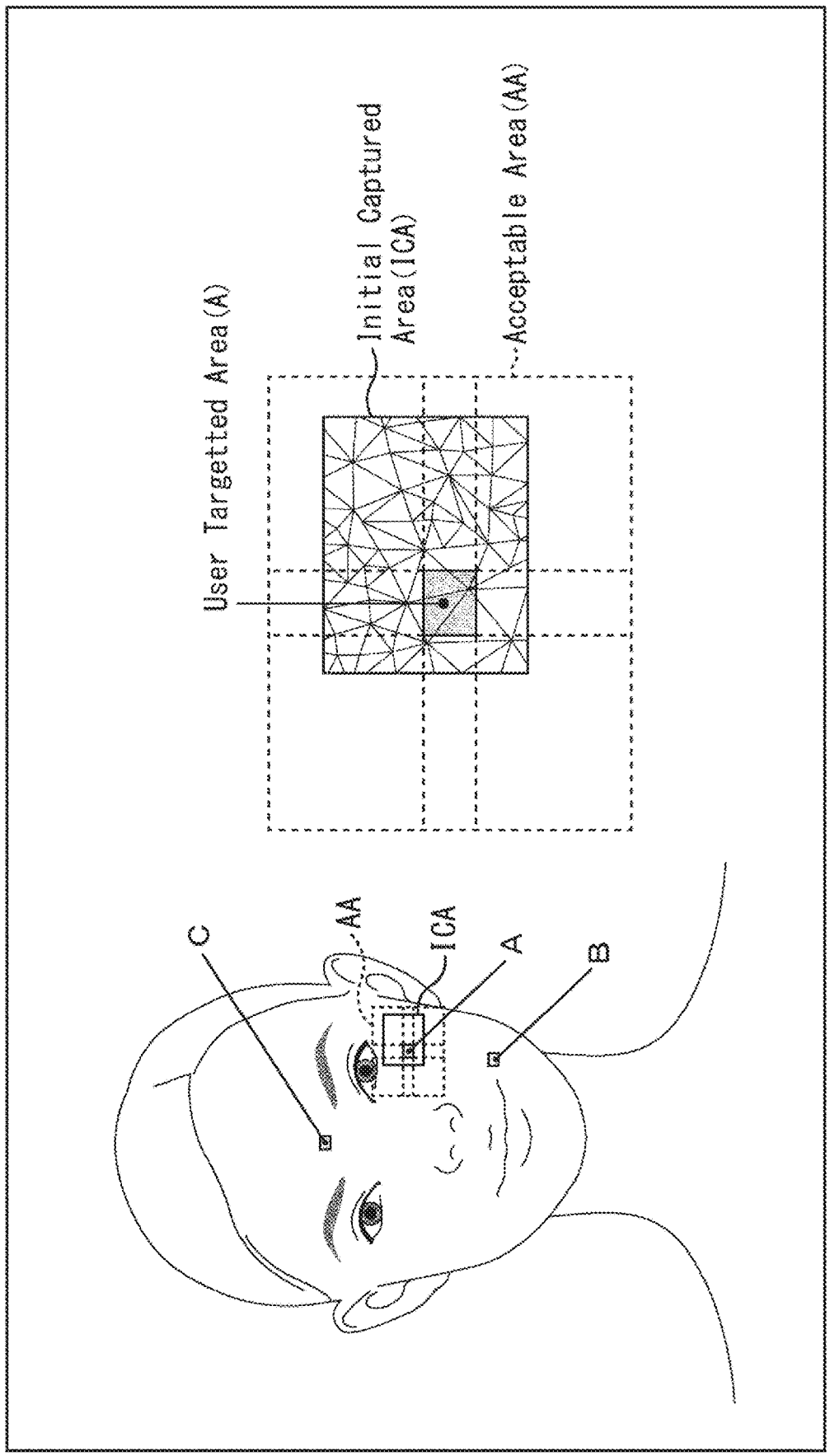
FIG. 19 is a diagram showing a display example for indicating a measurement optimal region.

FIG. 19 is a diagram showing a display example for indicating a measurement optimal region. In the display example of FIG. 19, on a schematically illustrated facial surface, frames A, B, and C for indicating a cheek, a mouth, and a forehead serving as measurement optimal regions are displayed. The user captures a skin epidermis image of his or her face by the skin measuring device 20 to use such frames A, B, and C as indicators. For example, in FIG. 19, since the epidermis image ("initial captured area (ICA)" of FIG. 19) captured by the skin measuring device 20 includes a measurement optimal region ("user targeted area (A)" of FIG. 19) of the cheek, an epidermis image including the measurement optimal region is captured. Regions surrounded by dotted lines of FIG. 19 indicate measurable acceptable ranges ("acceptable area (AA)" of FIG. 19). In addition, in the display example of FIG. 19, while a schematically illustrated facial surface is shown, an image of the user's face that is actually captured may be displayed.

Here, a distribution of skin texture is known as information for identifying an individual similarly to a fingerprint. Focusing thereon, matching of the measurement optimal region included in the epidermis image using the distribution of skin texture is performed. The epidermis image including at least the measurement optimal region for each user can be recorded in time series.

Figure 20:
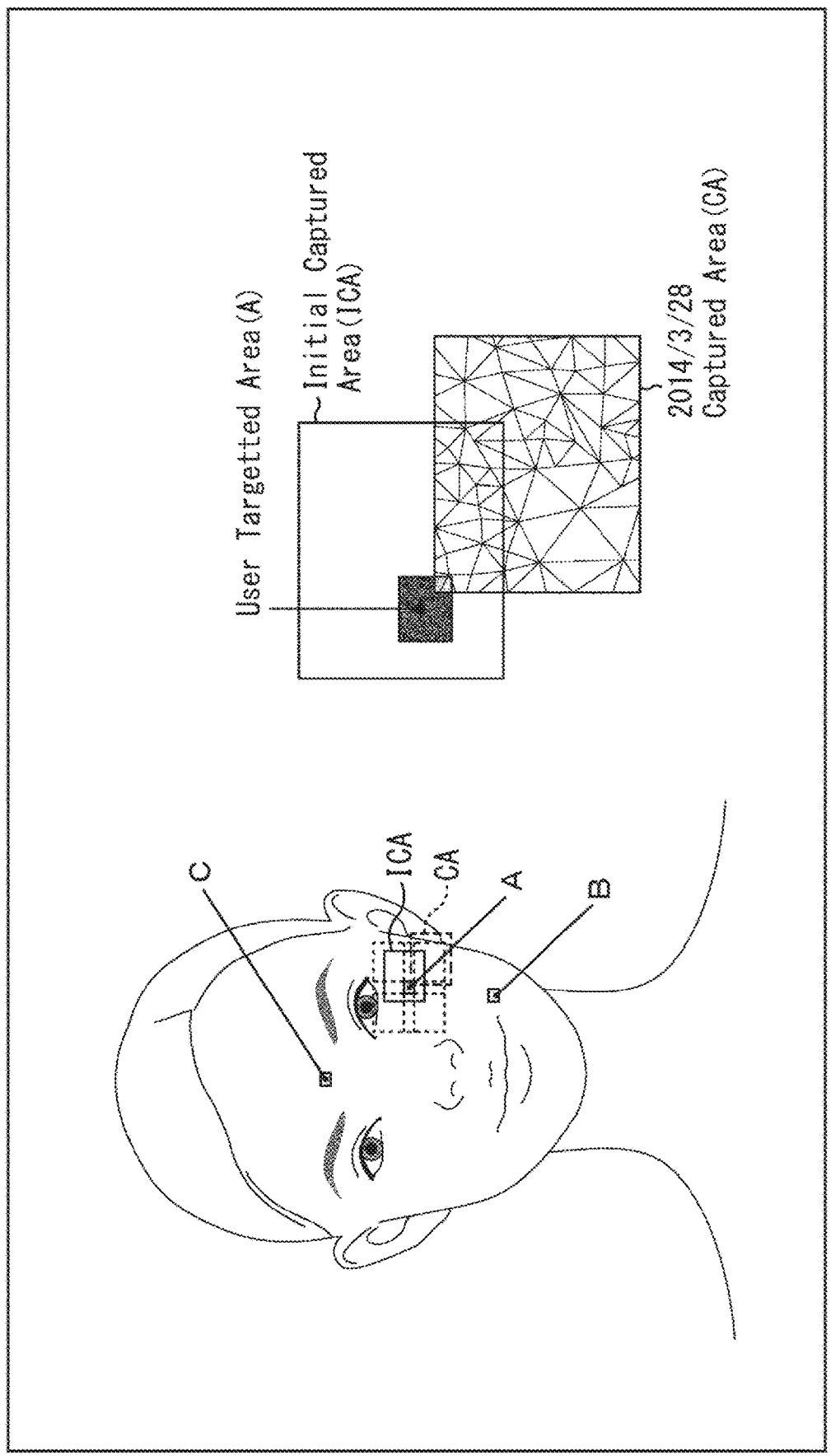
FIG. 20 is a diagram showing an example when epidermis images are recorded in time series.

For example, when the measurement optimal region of the cheek is included in an epidermis image ("initial captured area (ICA)" of FIG. 20) that is captured for the first time and an epidermis image ("Mar. 28, 2014 captured area (CA)" of FIG. 20) that is captured for the second time, matching of such measurement optimal regions is performed, and thus (the measurement optimal region included in) such epidermis images are recorded in association. When the skin is measured at predetermined measurement intervals, for example, on a daily basis or a weekly basis, (the measurement optimal region included in) the epidermis images captured at the measurement intervals are recorded in time series. For example, a matching process of the measurement optimal region is performed by the skin condition analysis unit 102, and an epidermis image including at least the measurement optimal region is recorded in a recording unit (not illustrated) included in the skin condition analysis unit 102.

In addition, the user sets a specific region on the facial surface recorded in the recording unit and an epidermis image corresponding to the region may be recorded in the recording unit. For example, without the analysis result image, a region of dark melasma and moles that can be visually recognized by the user is set to have top priority. Next, in this order of the analysis result image (for example, the analysis result images Q and R) using dark melasma and comedos as indicators, and the analysis result image (for example, the analysis result images S and T) indicating pore conditions, measurement is performed each time in an image-detected region, and the user can visually recognize (set) a specific region to be recorded in the recording unit.

Figure 21:
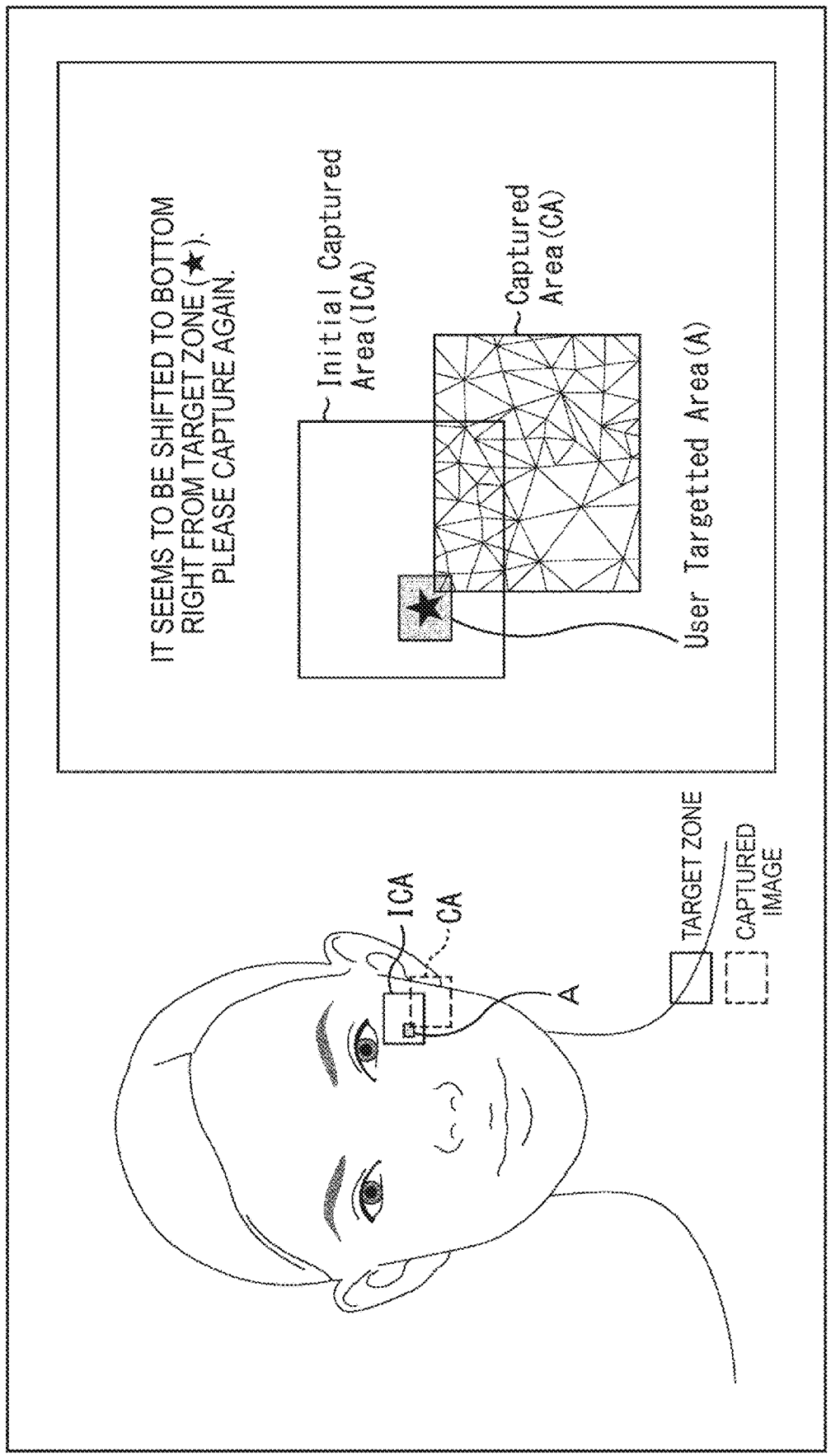
FIG. 21 is a diagram showing a display example of a message for guiding to an optimal imaging position.

In FIG. 20, since the epidermis image that is captured for the second time includes only a part of the measurement optimal region, an imaging position may be guided to include the entire region. For example, as shown in FIG. 21, when the epidermis image captured by the skin measuring device 20 includes a part of a target zone such as the measurement optimal region but does not include the entire zone, the skin measuring device 20 displays a message for guiding to an optimal imaging position, and capturing of an epidermis image including the entire measurement optimal region can be supported. That is, when the user captures the skin epidermis of the face, if a current imaging position is outside of the optimal imaging position, the display control unit 153 displays a message for guiding the current imaging position to the optimal imaging position.

Figure 22:
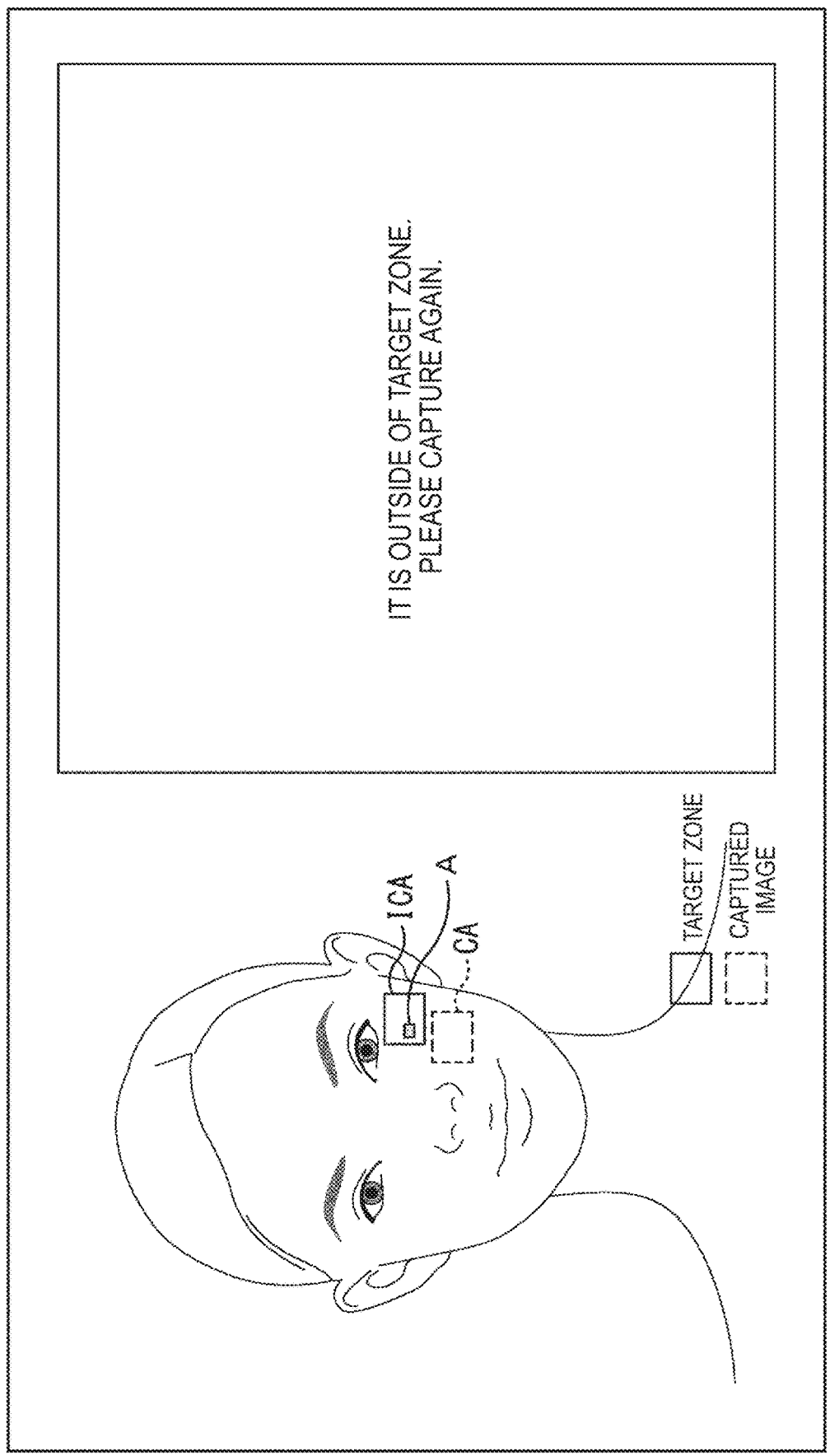
FIG. 22 is a diagram showing a display example of a message for indicating capturing again.

In addition, as shown in FIG. 22, when the epidermis image captured by the skin measuring device 20 does not include a target zone such as the optimal measurement region at all, a message indicating the fact is displayed, and it is possible to prompt to capture an epidermis image again. Here, when the user performs capturing using the skin measuring device 20 at an imaging position that is completely misguided, on a schematically illustrated facial surface, a distance from the target zone may be indicated using a schematically captured region as an indicator. That is, when the user captures the skin epidermis of the face, if a current imaging position is outside of the optimal imaging position, the display control unit 153 displays a distance from the current imaging position to the optimal imaging position.

In this manner, when a function of imaging navigation is provided, since the user measures the skin according to the imaging navigation, it is possible to increase accuracy of capturing (measuring) the epidermis image by the skin measuring device 20.

<5. Modification Example: Simplified Display Form>

Figure 23:
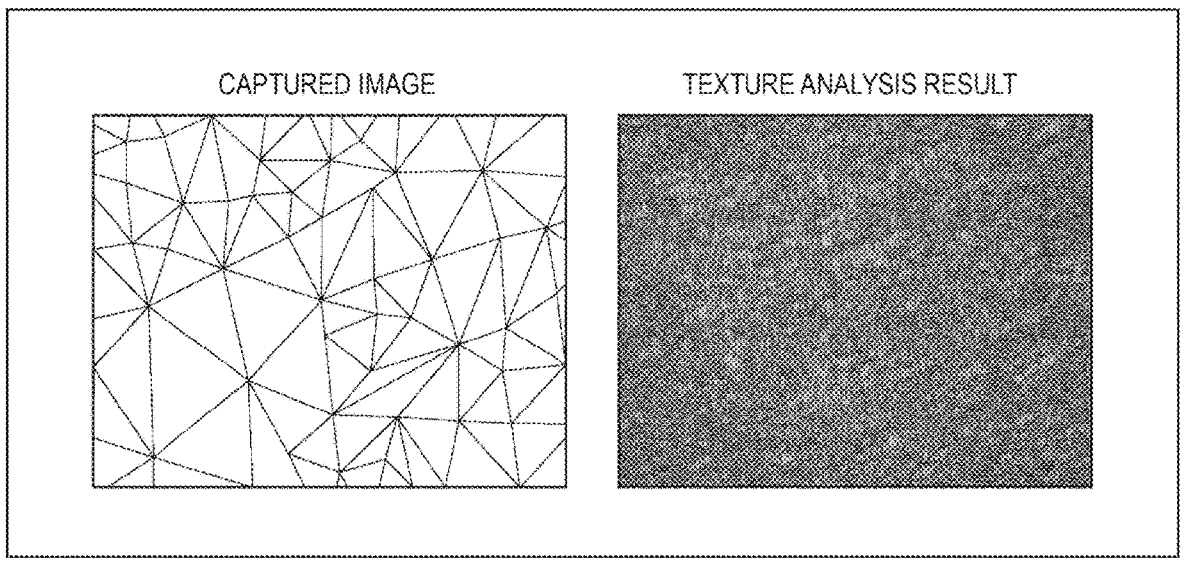
FIG. 23 is a diagram showing an analysis result image of another display form.
Figure 24:
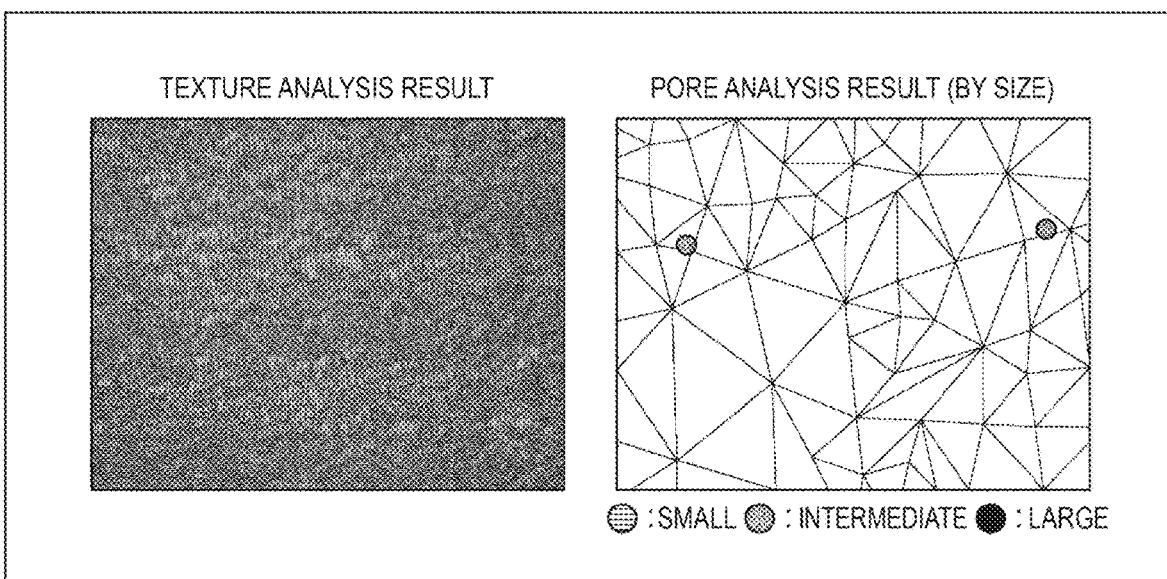
FIG. 24 is a diagram showing an analysis result image of another display form.

An example in which the analysis result image indicating skin conditions is described has been described. However, for example, as shown in FIG. 23, even when cristae cutis blocks adjacent through sulci cutis are separately expressed in a different color in a simple manner, since each cristae cutis can be visually recognized, it is possible to intuitively and visually recognize skin conditions. In addition, for example, as shown in FIG. 24, even when a size of a pore is separately expressed in a different color in a simple manner, since each pore can be visually recognized, it is possible to intuitively and visually recognize skin conditions.

<6. Other System Configurations>

While the skin analysis display system 1 of FIG. 1 has been described to include the terminal device 10 and the skin measuring device 20, a dedicated server is provided on the Internet and the server may implement some functions of the terminal device 10. Hereinafter, another configuration of the skin analysis display system will be described with reference to FIG. 25 to FIG. 27.

(Other Configuration 1 of Skin Analysis Display System)

Figure 25:
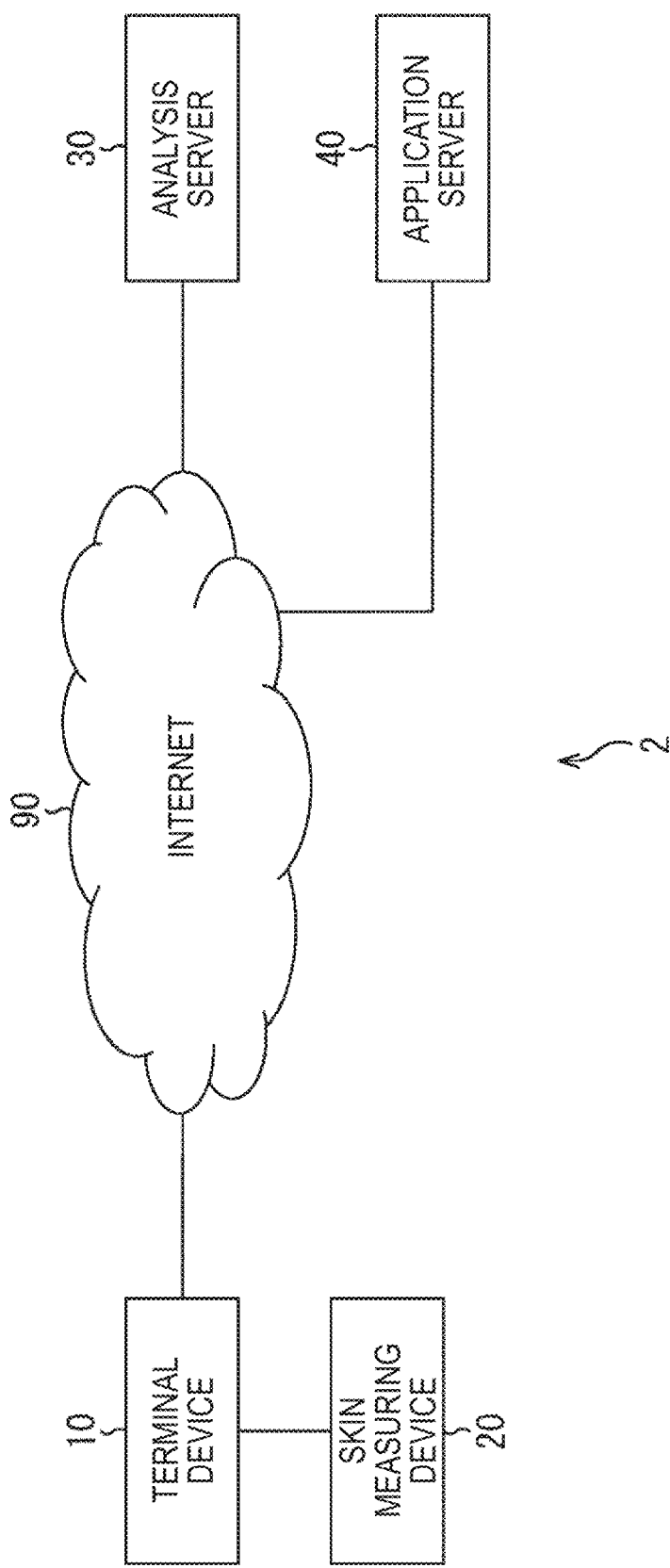
FIG. 25 is a diagram showing another configuration of an embodiment of the skin analysis display system to which the present technology is applied.

FIG. 25 is a diagram showing another configuration of an embodiment of the skin analysis display system to which the present technology is applied.

As shown in FIG. 25, a skin analysis display system 2 includes the terminal device 10, the skin measuring device 20, an analysis server 30, and an application server 40. However, the terminal device 10 and the skin measuring device 20 are connected through a cable that supports a predetermined standard. In addition, the terminal device 10 is connected to the analysis server 30 and the application server 40 via the Internet 90.

The terminal device 10 accesses the application server 40 via the Internet 90 and downloads an application. While the application is executed, the terminal device 10 transmits the captured image provided from the skin measuring device 20 to the analysis server 30 via the Internet 90.

The analysis server 30 performs an analysis process in which skin conditions are analyzed based on the captured image transmitted from the terminal device 10 via the Internet 90. The analysis server 30 transmits the skin condition analysis result obtained in the analysis process to the terminal device 10 via the Internet 90. The terminal device 10 receives and acquires the skin condition analysis result transmitted from the analysis server 30 via the Internet 90. The terminal device 10 generates an analysis result image of a predetermined display form based on the skin condition analysis result acquired from the analysis server 30 and displays the image on the display unit 104.

Figure 3:
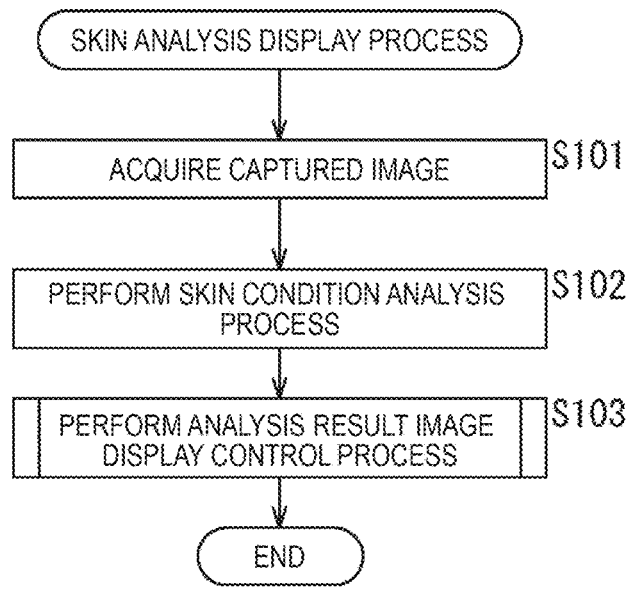
FIG. 3 is a flowchart describing a flow of a skin analysis display process performed by a terminal device.
Figure 4:
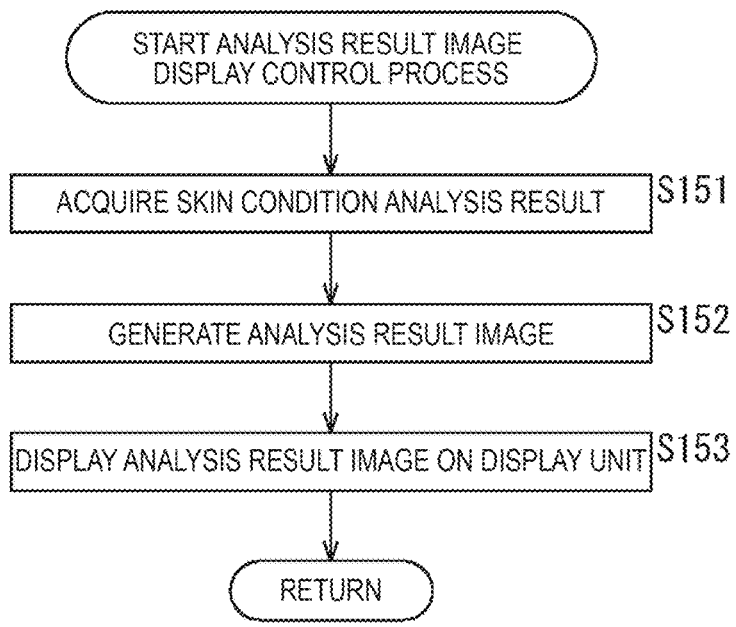
FIG. 4 is a flowchart describing details of an analysis result image display control process.

That is, in this case, when processes of the terminal device 10 and the analysis server 30 are allocated according to the flowchart of FIG. 3, the processes of Steps S101 and 103 are performed by the terminal device 10 and the process of Step S102 of FIG. 3 is performed by the analysis server 30.

In addition, after the analysis process in which skin conditions are analyzed is performed, the analysis server 30 generates an analysis result image of a predetermined display form based on the skin condition analysis result obtained in the analysis process and may transmit the image to the terminal device 10 via the Internet 90. In this case, the terminal device 10 receives the analysis result image transmitted from the analysis server 30 via the Internet 90 and displays the image on the display unit 104.

That is, in this case, when processes of the terminal device 10 and the analysis server 30 are allocated according to the flowchart of FIG. 3, the process of Step S101 is performed by the terminal device 10, and the processes of Steps S102 and 103 of FIG. 3 are performed by the analysis server 30. That is, in this case, the terminal device 10 displays the analysis result image on the display unit 104 under control of the analysis server 30.

As described above, in the skin analysis display system 2, since the analysis process and the like are concentrated at the analysis server 30, it is possible to reduce a processing load of the terminal device 10. In addition, even in the skin analysis display system 2, since information obtained from the skin analysis result in a predetermined display form is displayed on the display unit 104, the user can intuitively and visually recognize his or her skin conditions.

(Other Configuration 2 of Skin Analysis Display System)

Figure 26:
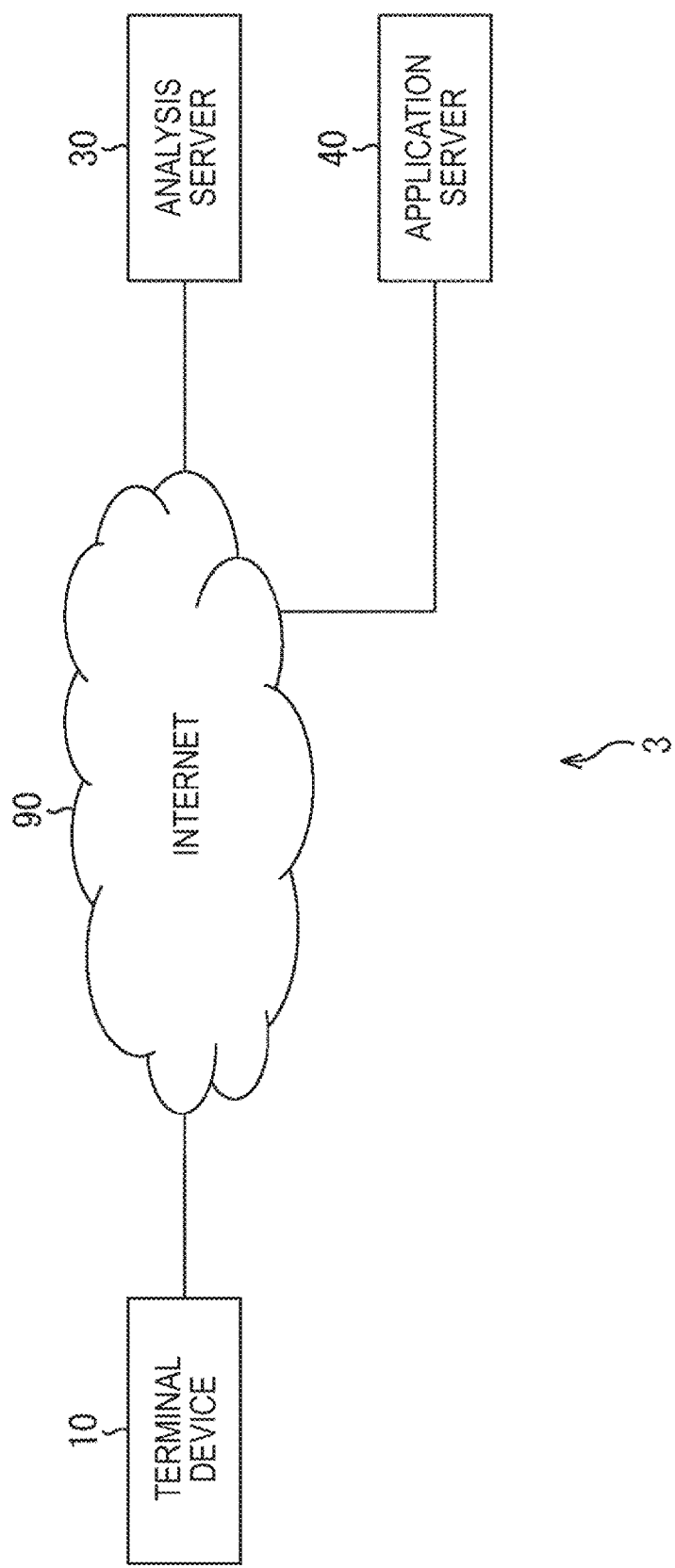
FIG. 26 is a diagram showing another configuration of an embodiment of the skin analysis display system to which the present technology is applied.

FIG. 26 is a diagram showing another configuration of an embodiment of the skin analysis display system to which the present technology is applied.

A skin analysis display system 3 of FIG. 26 is different from the skin analysis display system 2 of FIG. 25 in that the skin measuring device 20 is not connected to the terminal device 10. That is, the terminal device 10 of FIG. 26 does not acquire the captured image from the skin measuring device 20 but acquires the captured image obtained by capturing the skin epidermis of the user's face by the skin measurement unit (not illustrated) included therein. Then, the terminal device 10 transmits the captured image to the analysis server 30 via the Internet 90 and thus displays an analysis result image of a predetermined display form according to the skin condition analysis result obtained by the analysis server 30.

As described above, in the skin analysis display system 3, since the skin measuring device 20 is not connected, but the skin measurement unit included in the terminal device 10 is used, the user can save the time of preparing the skin measuring device 20. In addition, even in the skin analysis display system 3, since information obtained from the skin analysis result in a predetermined display form is displayed on the display unit 104, the user can intuitively and visually recognize his or her skin conditions.

(Other Configuration 3 of Skin Analysis Display System)

Figure 27:
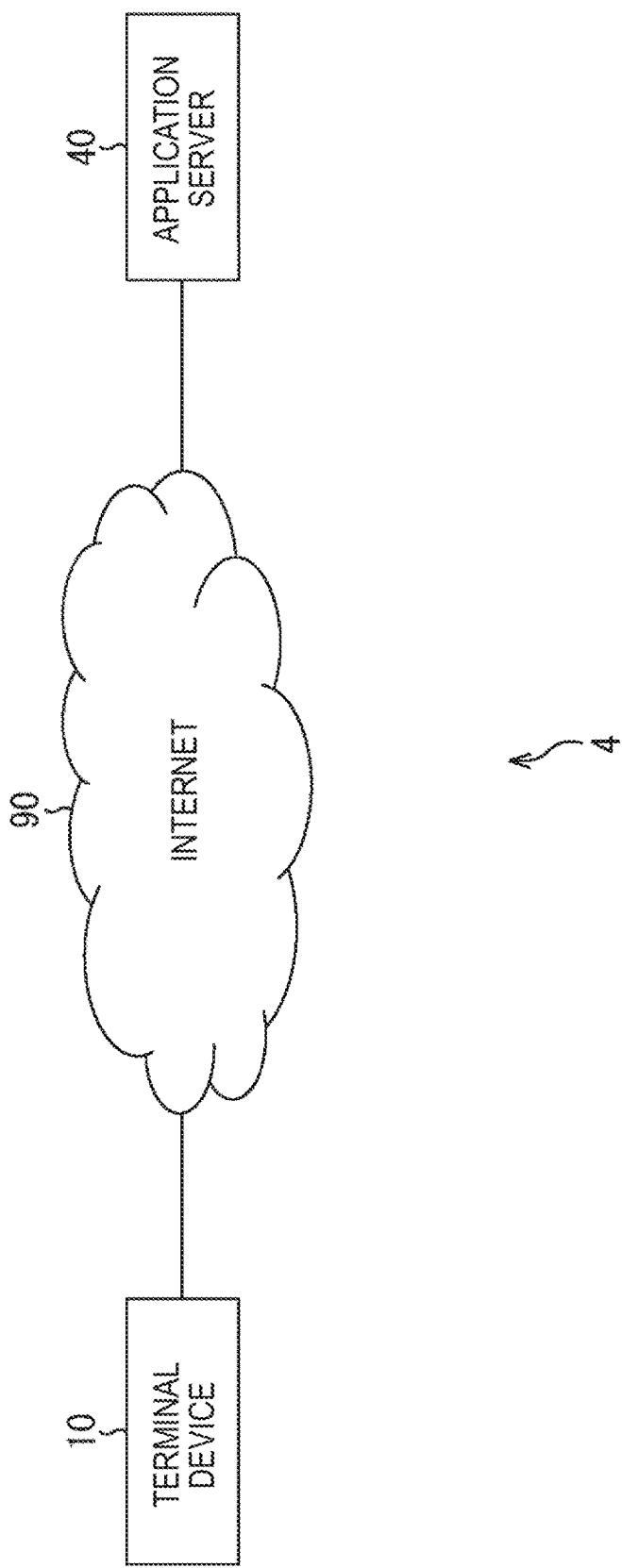
FIG. 27 is a diagram showing another configuration of an embodiment of the skin analysis display system to which the present technology is applied.

FIG. 27 is a diagram showing another configuration of an embodiment of a skin analysis display system to which the present technology is applied.

A skin analysis display system 4 of FIG. 27 is different from the skin analysis display system 3 of FIG. 26 in that the analysis server 30 is not connected to the Internet 90. In the skin analysis display system 4, the terminal device 10 accesses the application server 40 via the Internet 90, and downloads an application. While the application is executed, the terminal device 10 performs an analysis process in which skin conditions are analyzed based on the captured image that is captured by a skin measurement unit included therein. Then, the terminal device 10 generates an analysis result image of a predetermined display form based on the skin condition analysis result and displays the image on the display unit 104.

That is, in this case, the processes of Steps S101 to S103 of FIG. 3 are performed by the terminal device 10.

As described above, in the skin analysis display system 4, since the application is distributed from the application server 40 via the Internet 90, it is possible to easily support version upgrade of the application. In addition, in the skin analysis display system 4, since the skin measuring device 20 is not connected but the skin measurement unit included in the terminal device 10 is used, the user can save the time of preparing the skin measuring device 20. Further, even in the skin analysis display system 4, since information obtained from the skin analysis result in a predetermined display form is displayed on the display unit 104, the user can intuitively and visually recognize his or her skin conditions.

<7. Configuration of Computer>

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 28:
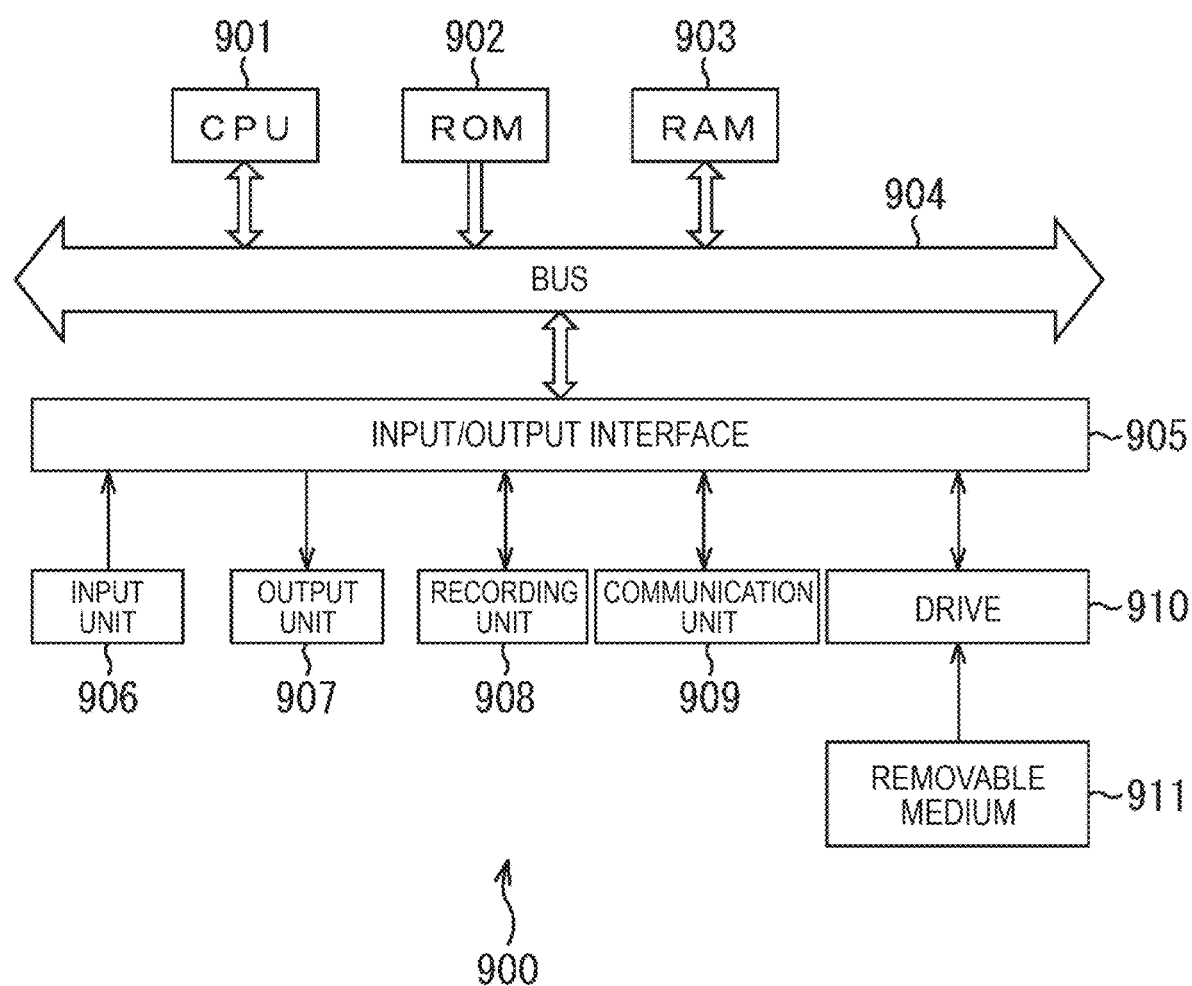
FIG. 28 is a diagram showing a configuration example of a computer.

FIG. 28 is a block diagram showing an example configuration of the hardware of a computer that executes the series of processes described earlier according to a program.

In a computer 900, a CPU (Central Processing Unit) 901, a ROM (Read Only Memory) 902, and a RAM (Random Access Memory) 903 are mutually connected by a bus 904. An input/output interface 905 is also connected to the bus 904. An input unit 906, an output unit 907, a recording unit 908, a communication unit 909, and a drive 910 are connected to the input/output interface 905.

The input unit 906 is configured from a keyboard, a mouse, a microphone or the like. The output unit 907 configured from a display, a speaker or the like. The recording unit 908 is configured from a hard disk, a non-volatile memory or the like. The communication unit 909 is configured from a network interface or the like. The drive 910 drives a removable medium 911 such as a magnetic disk, an optical disk, a magneto-optical disk, a semiconductor memory or the like.

In the computer 900 configured as described above, as one example the CPU 901 loads a program stored in the recording unit 908 via the input/output interface 905 and the bus 904 into the RAM 903 and executes the program to carry out the series of processes described earlier.

As one example, the program executed by the computer 900 (the CPU 901) may be provided by being recorded on the removable medium 911 as a packaged medium or the like. The program can also be provided via a wired or wireless transfer medium, such as a local area network, the Internet, or a digital satellite broadcast.

In the computer 900, by loading the removable medium 911 into the drive 910, the program can be installed into the recording unit 908 via the input/output interface 905. It is also possible to receive the program from a wired or wireless transfer medium using the communication unit 909 and install the program into the recording unit 908. As another alternative, the program can be installed in advance into the ROM 902 or the recording unit 908.

Note that the program executed by the computer 900 may be a program in which processes are carried out in a time series in the order described in this specification or may be a program in which processes are carried out in parallel or at necessary timing, such as when the processes are called.

Here, in the present specification, the processing step for describing a program causing the computer 900 to perform various kinds of processing is not necessarily processed in time series along the order illustrated as the flowchart, and may include processing performed in parallel or individually (e.g., parallel processing or processing by an object).

Furthermore, the program may be processed by a single computer or may be dispersively processed by a plurality of computers. Moreover, the program may be transferred to a remote computer and then executed.

Further, in the present disclosure, a system has the meaning of a set of a plurality of configured elements (such as an apparatus or a module (part)), and does not take into account whether or not all the configured elements are in the same casing. Therefore, the system may be either a plurality of apparatuses, stored in separate casings and connected through a network, or a plurality of modules within a single casing.

An embodiment of the disclosure is not limited to the embodiments described above, and various changes and modifications may be made without departing from the scope of the disclosure. For example, the present disclosure can adopt a configuration of cloud computing which processes by allocating and connecting one function by a plurality of apparatuses through a network.

Further, each step described by the above-mentioned flow charts can be executed by one apparatus or by allocating a plurality of apparatuses. In addition, in the case where a plurality of processes are included in one step, the plurality of processes included in this one step can be executed by one apparatus or by sharing a plurality of apparatuses.

Additionally, the present technology may also be configured as below.

(1)

An information processing apparatus including:

an acquisition unit configured to acquire a skin condition analysis result based on an epidermis image obtained by capturing skin epidermis; and a display control unit configured to display an analysis result image of a predetermined display form based on the skin condition analysis result on a display unit.

(2)

The information processing apparatus according to (1), wherein the display control unit displays the analysis result image of a display form in which cristae cutis blocks adjacent through sulci cutis are differently expressed according to a surface area of cristae cutis.

(3)

The information processing apparatus according to (2),
wherein the display control unit performs display such that the cristae cutis blocks are expressed in different colors of a same color family with different shades.

(4)

The information processing apparatus according to (2) or (3),
wherein the display control unit performs display such that a width of the sulcus cutis is indicated by a type of a line, and a depth of the sulcus cutis is indicated by a color shade.

(5)

The information processing apparatus according to (3),
wherein the display control unit performs display such that other skin conditions overlap the cristae cutis blocks that are expressed in different colors of a same color family with different shades.

(6)

The information processing apparatus according to (5),
wherein the display control unit performs display such that a distribution of pores further overlaps the cristae cutis blocks that are expressed in different colors of a same color family with different shades.

(7)

The information processing apparatus according to (6),
wherein the distribution of the pores is a distribution of clogged pores and a simple clogged pore and an acne risk serving as a cause of acne are expressed in different colors.

(8)

The information processing apparatus according to any one of (1) to (3),
wherein the display control unit displays the analysis result image of a display form in which cristae cutis blocks having a specific shape are differently expressed according to a shape of cristae cutis.

(9)

The information processing apparatus according to any one of (1) to (3),
wherein the display control unit displays the analysis result image of a display form in which a gradation is applied according to directionality of texture by cristae cutis.

(10)

The information processing apparatus according to (1),
wherein the display control unit displays the analysis result image of a display form in which a color or a symbol is applied according to directionality of texture by sulci cutis.

(11)

The information processing apparatus according to (1),
wherein the display control unit displays the analysis result image of a display form according to cross sections of sulci cutis and cristae cutis.

(12)

The information processing apparatus according to (1),
wherein the display control unit displays the analysis result image of a display form in which at least one of a clogged pore distribution, a pore opening distribution, and a comedo distribution is expressed in a plurality of levels with shades of a same color family.

(13)

The information processing apparatus according to (12),
wherein, in the clogged pore distribution, a simple clogged pore and an acne risk serving as a cause of acne are expressed in different colors.

(14)

The information processing apparatus according to (1),
wherein, when a user captures skin epidermis of a face, the display control unit displays information indicating a measurement optimal region that is a region suitable as a target of a skin condition analysis process on a facial surface.

(15)

The information processing apparatus according to (14), further including
a recording unit configured to perform matching of the measurement optimal region included in the epidermis image using a skin texture distribution obtained from the skin condition analysis result whenever the user captures the skin epidermis of a face, and record the epidermis image including at least the measurement optimal region in time series.

(16)

The information processing apparatus according to (15),
wherein the recording unit records the epidermis image according to settings performed by the user.

(17)

The information processing apparatus according to any one of (14) to (16),
wherein, when the user captures the skin epidermis of a face, if a current imaging position is outside of an optimal imaging position, the display control unit displays a message for showing the optimal imaging position from the current imaging position.

(18)

The information processing apparatus according to any one of (14) to (17),
wherein, when the user captures the skin epidermis of a face, if the current imaging position is outside of the optimal imaging position, the display control unit displays a distance from the current imaging position to the optimal imaging position.

(19)

An information processing method performed by an information processing apparatus, the method including:
acquiring a skin condition analysis result based on an epidermis image obtained by capturing skin epidermis; and
displaying an analysis result image of a predetermined display form on a display unit on the basis of the skin condition analysis result.

(20)

A program for causing a computer to function as:
an acquisition unit configured to acquire a skin condition analysis result based on an epidermis image obtained by capturing skin epidermis; and
a display control unit configured to display an analysis result image of a predetermined display form based on the skin condition analysis result on a display unit.

REFERENCE SIGNS LIST 1, 2, 3, 4 skin analysis display system
10 terminal device
20 skin measurement unit
30 analysis server
40 application server
90 the Internet
101 captured image acquisition unit
102 skin condition analysis unit
103 analysis result image display control unit
104 display unit
151 analysis result acquisition unit
152 analysis result image generation unit
153 display control unit
900 computer
901 CPU

The invention claimed is:

1. An information processing apparatus comprising:
a processing device and a memory containing instructions that, when executed by the processing device, implement:
an acquisition unit configured to acquire a skin condition analysis result based on an epidermis image obtained by capturing skin epidermis;
a display control unit configured to display an analysis result image of a predetermined display form based on the skin condition analysis result on a display unit, wherein cristae cutis blocks having an area greater than a predetermined threshold value are shown on the analysis result image as cristae cutis blocks of a first color and cristae cutis blocks having an area less than the predetermined threshold value are shown on the analysis result image as cristae cutis blocks of a second color, wherein the display control unit is configured to indicate on the analysis result image a width of sulcus cutis by a width of a line that represents the sulcus cutis and to indicate on the analysis result image a depth of the sulcus cutis by a shade of the line that represents the sulcus cutis, and wherein, when a user captures skin epidermis of a face, the display control unit is configured to display information indicating a measurement optimal region that is a region suitable as a target of a skin condition analysis process on a facial surface; and
a recording unit configured to perform matching of the measurement optimal region included in the epidermis image using a skin texture distribution obtained from the skin condition analysis result whenever the user captures the skin epidermis of the face, and to record the epidermis image including at least the measurement optimal region in time series.

2. The information processing apparatus according to claim 1,
wherein the display control unit is configured to display the cristae cutis blocks in different colors of a same color family with different shades.

3. The information processing apparatus according to claim 2,
wherein the display control unit is configured to display other skin conditions overlapping the cristae cutis blocks that are expressed in different colors of a same color family with different shades.

4. The information processing apparatus according to claim 3,
wherein the display control unit is configured to display a distribution of pores further overlapping the cristae cutis blocks that are expressed in different colors of a same color family with different shades.

5. The information processing apparatus according to claim 4,
wherein the distribution of the pores is a distribution of clogged pores and a simple clogged pore and an acne risk serving as a cause of acne are expressed in different colors.

6. The information processing apparatus according to claim 1,
wherein the display control unit is configured to display the analysis result image of the display form in which cristae cutis blocks having a specific shape are differently expressed according to a shape of cristae cutis.

7. The information processing apparatus according to claim 1,
wherein the display control unit is configured to display the analysis result image of the display form in which a gradation is applied according to directionality of texture by cristae cutis.

8. The information processing apparatus according to claim 1,
wherein the display control unit is configured to display the analysis result image of the display form in which a color or a symbol is applied according to directionality of texture by sulci cutis.

9. The information processing apparatus according to claim 1,
wherein the display control unit is configured to display the analysis result image of the display form according to cross sections of sulci cutis and cristae cutis.

10. The information processing apparatus according to claim 1,
wherein the display control unit is configured to display the analysis result image of the display form in which at least one of a clogged pore distribution, a pore opening distribution, and a comedo distribution is expressed in a plurality of levels with shades of a same color family.

11. The information processing apparatus according to claim 10,
wherein, in the clogged pore distribution, a simple clogged pore and an acne risk serving as a cause of acne are expressed in different colors.

12. The information processing apparatus according to claim 1,
wherein the recording unit is configured to record the epidermis image according to settings performed by the user.

13. The information processing apparatus according to claim 12,
wherein, when the user captures the skin epidermis of the face and when a current imaging position is outside of an optimal imaging position, the display control unit is configured to display a message for showing the optimal imaging position from the current imaging position.

14. The information processing apparatus according to claim 13,
wherein, when the user captures the skin epidermis of the face and when the current imaging position is outside of the optimal imaging position, the display control unit is configured to display the current imaging position and the optimal imaging position.

15. An information processing method performed by an information processing apparatus, the method comprising:
acquiring a skin condition analysis result based on an epidermis image obtained by capturing skin epidermis;
displaying an analysis result image of a predetermined display form on a display unit on the basis of the skin condition analysis result, wherein cristae cutis blocks having an area greater than a predetermined threshold value are shown on the analysis result image as cristae cutis blocks of a first color and cristae cutis blocks having an area less than the predetermined threshold value are shown on the analysis result image as cristae cutis blocks of a second color, wherein a width of sulcus cutis is indicated on the analysis result image by a width of a line that represents the sulcus cutis and a depth of the sulcus cutis is indicated on the analysis result image by a shade of the line that represents the sulcus cutis, and wherein, when a user captures skin epidermis of a face, information indicating a measurement optimal region that is a region suitable as a target of a skin condition analysis process on a facial surface is displayed; and matching of the measurement optimal region included in the epidermis image using a skin texture distribution obtained from the skin condition analysis result whenever the user captures the skin epidermis of the face, and recording the epidermis image including at least the measurement optimal region in time series.

16. A non-transitory, computer-readable medium containing instructions that, when executed by a processing device, perform an information processing method comprising:

acquiring a skin condition analysis result based on an epidermis image obtained by capturing skin epidermis;

displaying an analysis result image of a predetermined display form based on the skin condition analysis result on a display unit, wherein cristae cutis blocks having an area greater than a predetermined threshold value are shown on the analysis result image as cristae cutis blocks of a first color and cristae cutis blocks having an area less than the predetermined threshold value are shown on the analysis result image as cristae cutis blocks of a second color wherein a width of sulcus cutis is indicated on the analysis result image by a width of a line that represents the sulcus cutis and a depth of the sulcus cutis is indicated on the analysis result image by a shade of the line that represents the sulcus cutis, and wherein, when a user captures skin epidermis of a face, information indicating a measurement optimal region that is a region suitable as a target of a skin condition analysis process on a facial surface is displayed; and matching of the measurement optimal region included in the epidermis image using a skin texture distribution obtained from the skin condition analysis result whenever the user captures the skin epidermis of the face, and recording the epidermis image including at least the measurement optimal region in time series.

* * * * *